United States Patent
Gjerset et al.

(10) Patent No.: US 8,431,353 B2
(45) Date of Patent: Apr. 30, 2013

(54) METHODS AND COMPOSITIONS FOR TOPOISOMERASE I MODULATED TUMOR SUPPRESSION

(75) Inventors: Ruth A. Gjerset, San Diego, CA (US); Keya Bandyopadhyay, San Diego, CA (US)

(73) Assignee: RG Biopharma LLC, San Diego, CA (US)

( * ) Notice: Subject to any disclaimer, the term of this patent is extended or adjusted under 35 U.S.C. 154(b) by 243 days.

(21) Appl. No.: 12/898,872

(22) Filed: Oct. 6, 2010

(65) Prior Publication Data

US 2011/0136850 A1    Jun. 9, 2011

Related U.S. Application Data

(63) Continuation-in-part of application No. 12/377,498, filed as application No. PCT/US2007/018387 on Aug. 16, 2007.

(60) Provisional application No. 60/822,774, filed on Aug. 18, 2006.

(51) Int. Cl.
*G01N 33/574* (2006.01)
*C12Q 1/00* (2006.01)
*A01N 43/42* (2006.01)

(52) U.S. Cl.
USPC .............................. 435/7.23; 435/4; 514/283

(58) Field of Classification Search ............. 435/4, 7.23; 514/283
See application file for complete search history.

(56) References Cited

U.S. PATENT DOCUMENTS

2011/0028536 A1* 2/2011 Gjerset et al. ............... 514/44 R

OTHER PUBLICATIONS

Bandyopadhyay et al. (PLoS One, Nov. 2012, 7(11): e50427).*

* cited by examiner

*Primary Examiner* — Misook Yu
*Assistant Examiner* — Yan Xiao

(57) ABSTRACT

Disclosed herein are methods and compositions for determining the sensitivity or enhancing the sensitivity of cells to the effects of topoisomerase I inhibitors. Also disclosed are methods and compositions for inducing cell death, apoptosis and/or growth arrest which may be used for tumor suppression.

6 Claims, 14 Drawing Sheets

A  pull-down (silver stain)
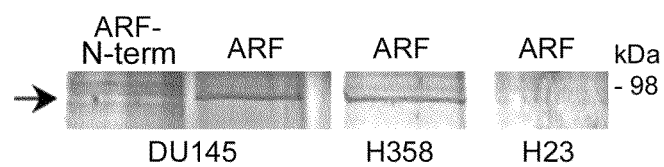
B  pull-down (Western)
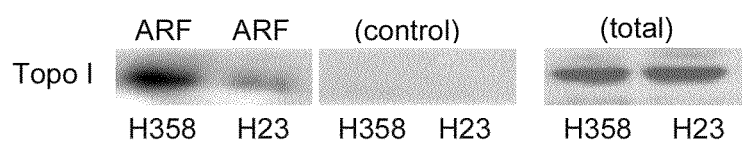
C  IP: Topo I
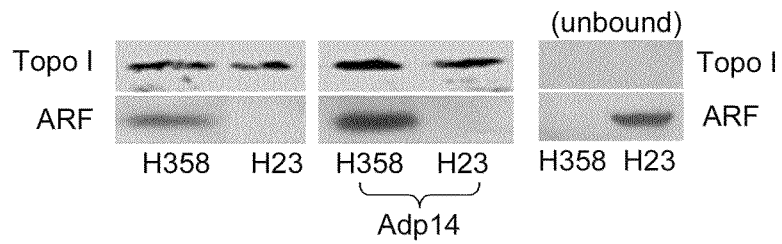
Figure 1

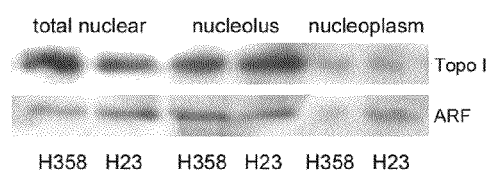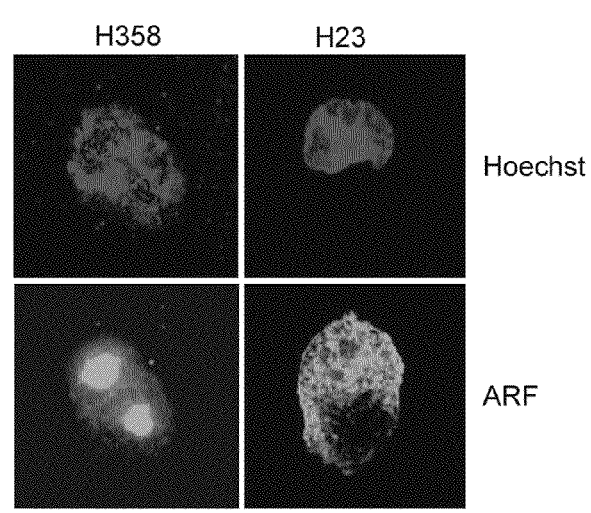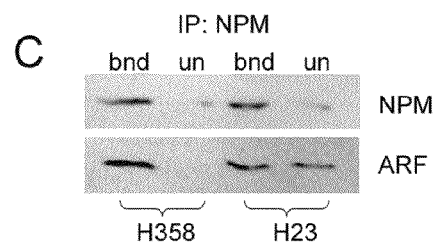
Figure 4

Figure 9

```
1    mgrgrcvgps  lqlrgqewrc  splvpkggaa  aaelgpggge  nmvrrflvtl  rirracgppr
61   vrvfvvhipr  ltgewaapga  paavalvlml  lrsqrlgqqp  lprrpghddg  qrpsggaaaa
121  prrgaqlrrp  rhshptrarr  cpgglpghag  gaapgrgaag  rarclgpsar  gpg
```

(SEQ ID NO: 2)

Figure 10

```
1    msgdhlhnds  qieadfrlnd  shkhkdkhkd  rehrhkehkk  ekdrekskhs  nsehkdsekk
61   hkekektkhk  dgssekhkdk  hkdrdkekrk  eekvrasgda  kikkekengf  ssppqikdep
121  eddgyfvppk  edikplkrpr  deddadykpk  kiktedtkke  kkrkleeeed  gklkkpknkd
181  kdkkvpepdn  kkkkpkkeee  qkwkwweeer  ypegikwkfl  ehkgpvfapp  yeplpenvkf
241  yydgkvmkls  pkaeevatff  akmldheytt  keifrknffk  dwrkemtnee  kniitnlskc
301  dftqmsqyfk  aqtearkqms  keeklkikee  nekllkeygf  cimdnhkeri  anfkieppgl
361  frgrgnhpkm  gmlkrrimpe  diiincskda  kvpspppghk  wkevrhdnkv  twlvswteni
421  qgsikyimln  pssrikgekd  wqkyetarrl  kkcvdkirnq  yredwkskem  kvrqravaly
481  fidklalrag  nekeegetad  tvgccslrve  hinlhpeldg  qeyvvefdfl  gkdsiryynk
541  vpvekrvfkn  lqlfmenkqp  eddlfdrlnt  gilnkhlqdl  megltakvfr  tynasitlqq
600  qlkeltapde  nipakilsyn  ranravailc  nhqrappktf  eksmmnlqtk  idakkeqlad
661  arrdlksaka  dakvmkdakt  kkvveskkka  vqrleeqlmk  levqatdree  nkqialgtsk
721  lnyldpritv  awckkwgvpi  ekiynktqre  kfawaidmad  edyef
```

(SEQ ID NO: 3)

SEQUENCE LISTING

```
<160> NUMBER OF SEQ ID NOS: 8

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Lys Arg Pro Ser Gln Arg Ser Lys Tyr Leu
1               5                   10

<210> SEQ ID NO 2
<211> LENGTH: 173
<212> TYPE: PRT
<213> ORGANISM: Homo sapiens

<400> SEQUENCE: 2

Met Gly Arg Gly Arg Cys Val Gly Pro Ser Leu Gln Leu Arg Gly Gln
1               5                   10                  15

Glu Trp Arg Cys Ser Pro Leu Val Pro Lys Gly Gly Ala Ala Ala Ala
                20                  25                  30

Glu Leu Gly Pro Gly Gly Glu Asn Met Val Arg Arg Phe Leu Val
            35                  40                  45

Thr Leu Arg Ile Arg Arg Ala Cys Gly Pro Pro Arg Val Arg Val Phe
        50                  55                  60

Val Val His Ile Pro Arg Leu Thr Gly Glu Trp Ala Ala Pro Gly Ala
65                  70                  75                  80

Pro Ala Ala Val Ala Leu Val Leu Met Leu Leu Arg Ser Gln Arg Leu
                85                  90                  95

Gly Gln Gln Pro Leu Pro Arg Arg Pro Gly His Asp Asp Gly Gln Arg
                100                 105                 110

Pro Ser Gly Gly Ala Ala Ala Pro Arg Arg Gly Ala Gln Leu Arg
            115                 120                 125

Arg Pro Arg His Ser His Pro Thr Arg Ala Arg Arg Cys Pro Gly Gly
        130                 135                 140

Leu Pro Gly His Ala Gly Gly Ala Ala Pro Gly Arg Gly Ala Ala Gly
145                 150                 155                 160

Arg Ala Arg Cys Leu Gly Pro Ser Ala Arg Gly Pro Gly
                165                 170

<210> SEQ ID NO 3
<211> LENGTH: 765
<212> TYPE: PRT
<213> ORGANISM: Homo sapiens

<400> SEQUENCE: 3

Met Ser Gly Asp His Leu His Asn Asp Ser Gln Ile Glu Ala Asp Phe
1               5                   10                  15

Arg Leu Asn Asp Ser His Lys His Lys Asp Lys His Lys Asp Arg Glu
                20                  25                  30
```

-continued

```
His Arg His Lys Glu His Lys Lys Glu Lys Asp Arg Glu Lys Ser Lys
         35                  40                  45
His Ser Asn Ser Glu His Lys Asp Ser Glu Lys Lys His Lys Glu Lys
 50                  55                  60
Glu Lys Thr Lys His Lys Asp Gly Ser Ser Glu Lys His Lys Asp Lys
 65                  70                  75                  80
His Lys Asp Arg Asp Lys Glu Lys Arg Lys Glu Glu Lys Val Arg Ala
                 85                  90                  95
Ser Gly Asp Ala Lys Ile Lys Lys Glu Lys Glu Asn Gly Phe Ser Ser
                100                 105                 110
Pro Pro Gln Ile Lys Asp Glu Pro Glu Asp Gly Tyr Phe Val Pro
             115                 120                 125
Pro Lys Glu Asp Ile Lys Pro Leu Lys Arg Pro Arg Asp Glu Asp Asp
130                 135                 140
Ala Asp Tyr Lys Pro Lys Lys Ile Lys Thr Glu Asp Thr Lys Lys Glu
145                 150                 155                 160
Lys Lys Arg Lys Leu Glu Glu Glu Asp Gly Lys Leu Lys Lys Pro
             165                 170                 175
Lys Asn Lys Asp Lys Asp Lys Lys Val Pro Glu Pro Asp Asn Lys Lys
             180                 185                 190
Lys Lys Pro Lys Lys Glu Glu Glu Gln Lys Trp Lys Trp Trp Glu Glu
             195                 200                 205
Glu Arg Tyr Pro Glu Gly Ile Lys Trp Lys Phe Leu Glu His Lys Gly
         210                 215                 220
Pro Val Phe Ala Pro Pro Tyr Glu Pro Leu Pro Glu Asn Val Lys Phe
225                 230                 235                 240
Tyr Tyr Asp Gly Lys Val Met Lys Leu Ser Pro Lys Ala Glu Glu Val
                 245                 250                 255
Ala Thr Phe Phe Ala Lys Met Leu Asp His Glu Tyr Thr Thr Lys Glu
                 260                 265                 270
Ile Phe Arg Lys Asn Phe Phe Lys Asp Trp Arg Lys Glu Met Thr Asn
             275                 280                 285
Glu Glu Lys Asn Ile Ile Thr Asn Leu Ser Lys Cys Asp Phe Thr Gln
290                 295                 300
Met Ser Gln Tyr Phe Lys Ala Gln Thr Glu Ala Arg Lys Gln Met Ser
305                 310                 315                 320
Lys Glu Glu Lys Leu Lys Ile Lys Glu Glu Asn Glu Lys Leu Leu Lys
                 325                 330                 335
Glu Tyr Gly Phe Cys Ile Met Asp Asn His Lys Glu Arg Ile Ala Asn
             340                 345                 350
Phe Lys Ile Glu Pro Pro Gly Leu Phe Arg Gly Arg Gly Asn His Pro
         355                 360                 365
Lys Met Gly Met Leu Lys Arg Arg Ile Met Pro Glu Asp Ile Ile Ile
370                 375                 380
Asn Cys Ser Lys Asp Ala Lys Val Pro Ser Pro Pro Gly His Lys
385                 390                 395                 400
Trp Lys Glu Val Arg His Asp Asn Lys Val Thr Trp Leu Val Ser Trp
                 405                 410                 415
Thr Glu Asn Ile Gln Gly Ser Ile Lys Tyr Ile Met Leu Asn Pro Ser
             420                 425                 430
Ser Arg Ile Lys Gly Glu Lys Asp Trp Gln Lys Tyr Glu Thr Ala Arg
         435                 440                 445
Arg Leu Lys Lys Cys Val Asp Lys Ile Arg Asn Gln Tyr Arg Glu Asp
         450                 455                 460
```

```
Trp Lys Ser Lys Glu Met Lys Val Arg Gln Arg Ala Val Ala Leu Tyr
465                 470                 475                 480

Phe Ile Asp Lys Leu Ala Leu Arg Ala Gly Asn Glu Lys Glu Glu Gly
            485                 490                 495

Glu Thr Ala Asp Thr Val Gly Cys Cys Ser Leu Arg Val Glu His Ile
        500                 505                 510

Asn Leu His Pro Glu Leu Asp Gly Gln Glu Tyr Val Val Glu Phe Asp
    515                 520                 525

Phe Leu Gly Lys Asp Ser Ile Arg Tyr Tyr Asn Lys Val Pro Val Glu
530                 535                 540

Lys Arg Val Phe Lys Asn Leu Gln Leu Phe Met Glu Asn Lys Gln Pro
545                 550                 555                 560

Glu Asp Asp Leu Phe Asp Arg Leu Asn Thr Gly Ile Leu Asn Lys His
                565                 570                 575

Leu Gln Asp Leu Met Glu Gly Leu Thr Ala Lys Val Phe Arg Thr Tyr
                580                 585                 590

Asn Ala Ser Ile Thr Leu Gln Gln Gln Leu Lys Glu Leu Thr Ala Pro
            595                 600                 605

Asp Glu Asn Ile Pro Ala Lys Ile Leu Ser Tyr Asn Arg Ala Asn Arg
610                 615                 620

Ala Val Ala Ile Leu Cys Asn His Gln Arg Ala Pro Pro Lys Thr Phe
625                 630                 635                 640

Glu Lys Ser Met Met Asn Leu Gln Thr Lys Ile Asp Ala Lys Lys Glu
                645                 650                 655

Gln Leu Ala Asp Ala Arg Arg Asp Leu Lys Ser Ala Lys Ala Asp Ala
                660                 665                 670

Lys Val Met Lys Asp Ala Lys Thr Lys Val Val Glu Ser Lys Lys
                675                 680                 685

Lys Ala Val Gln Arg Leu Glu Glu Gln Leu Met Lys Leu Glu Val Gln
690                 695                 700

Ala Thr Asp Arg Glu Glu Asn Lys Gln Ile Ala Leu Gly Thr Ser Lys
705                 710                 715                 720

Leu Asn Tyr Leu Asp Pro Arg Ile Thr Val Ala Trp Cys Lys Lys Trp
                725                 730                 735

Gly Val Pro Ile Glu Lys Ile Tyr Asn Lys Thr Gln Arg Glu Lys Phe
                740                 745                 750

Ala Trp Ala Ile Asp Met Ala Asp Glu Asp Tyr Glu Phe
            755                 760                 765

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
ggguuuucgu gguucacaut t                                            21

<210> SEQ ID NO 5
<211> LENGTH: 21
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
augugaacca cgaaaaccct c                                                   21

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Arg Arg Asp Asp Asp Ser Asp Asp Asp
1               5                   10

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Cys(Acm)
<220> FEATURE:
<221> NAME/KEY: MOD_RES
<222> LOCATION: (6)..(6)
<223> OTHER INFORMATION: pSer
<220> FEATURE:
<223> OTHER INFORMATION: N-term H; C-term NH2

<400> SEQUENCE: 7

Thr Val Gly Cys Cys Ser Leu Arg Val Glu His Ile Asn Leu His Pro
1               5                   10                  15

Glu Leu Lys Lys Cys
            20

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Lys Arg Thr Leu Arg Arg Leu
1               5
```

METHODS AND COMPOSITIONS FOR TOPOISOMERASE I MODULATED TUMOR SUPPRESSION

CROSS-REFERENCE TO RELATED APPLICATIONS

This application is a continuation in part of application Ser. No. 12/377,498, filed Aug. 6, 2010, which is a 35 USC 371 National Phase Entry Application from PCT/US07/018,387, filed Aug. 16, 2007, and designating the U.S., which claims the priority of U.S. Provisional Application No. 60/822,774 filed Aug. 18, 2006, the disclosures of which are incorporated herein by reference in their entireties.

RIGHTS IN THE INVENTION

This invention was supported in part by grants from the NIH/NCI (CA 111868, CA 135369) and from the California Tobacco-Related Disease Research Program (11RT-0074). The Government may have certain rights in this invention.

SEQUENCE LISTING

The instant application contains a Sequence Listing which has been submitted in ASCII format via EFS-Web and is hereby incorporated by reference in its entirety. Said ASCII copy, created on Feb. 8, 2011, is named 63890401.txt and is 10,332 bytes in size.

FIELD OF INVENTION

This invention relates to the field of cancer therapy and diagnostics.

BACKGROUND OF INVENTION

The following discussion of the background of the invention is merely provided to aid the reader in understanding the invention and is not admitted to describe or constitute prior art to the present invention.

Topoisomerase I is a nuclear enzyme that plays an important role in cell proliferation. The enzyme catalyzes the uncoiling of DNA during replication and transcription (Pommier, et al., Biochim Biophys Acta 1998; 1400(1-3):83-105; Wang, Annu Rev Biochem 1996; 65:635-92).

The activity of topoisomerase I is regulated by phosphorylation. Such phosphorylation occurs primarily on serine residues (Turman, et al., Biochem Med Metab Biol 1993; 50(2): 210-25; Coderoni, et al., Int J Biochem 1990; 22(7):737-46; Kaiserman, et al., Biochemistry 1988; 27(9):3216-22; Samuels, et al., J Biol Chem 1992; 267(16):11156-62) and appears to be necessary for the initial complex formation between the enzyme and the DNA (Coderoni, et al., Int J Biochem 1990; 22(7):737-46).

Human cancers are characterized by uncontrolled proliferation of abnormal cells. Topoisomerase I inhibitors have been used as chemotherapeutic agents that interfere with normal DNA replication and cell division. However, some cancers are not sensitive to such topoisomerase I inhibitors.

SUMMARY OF THE INVENTION

The present invention provides methods (and related compositions) for increasing the sensitivity of cells (e.g., cancer cells) to the activity of topoisomerase I inhibitors. The invention also provides methods for inducing growth arrest and/or cell death in cells (e.g., cancer cells). Further, the invention provides methods for determining the sensitivity of a cell (e.g., a cancer cell) to the effects of a topoisomerase I inhibitor.

The invention is based upon the discovery that cells resistant to topoisomerase inhibitors frequently have a deficiency in topoisomerase I serine phosphorylation, rendering them less sensitive (or insensitive) to the cytotoxic effect of topoisomerase I inhibitors. The deficiency in topoisomerase I phosphorylation reduces the ability of topoisomerase I to bind p14ARF (ARF), an activator protein. Thus, cancer cells can be assessed for their sensitivity to topoisomerase I inhibitors, prior to initiating therapy, by measuring the level of serine phosphorylation of topoisomerase I, its activity, and/or its ability to bind ARF. Likewise, cells can be sensitized to the effects of topoisomerase I inhibitors by increasing the amount of serine phosphorylation of topoisomerase I, or by increasing ARF-topoisomerase I complex formation by increasing, for example, the amount of ARF available for complexation with serine phosphorylated topoisomerase I.

An additional feature of the invention is the discovery that cell death and/or growth arrest may be induced by disrupting ARF-topoisomerase I complex formation. It is believed that free ARF, released from the ARF-topoisomerase I complexes, increases the biological activity of p53 (a known tumor suppressor gene) by sequestering HDM2, a p53 inhibitor.

Accordingly, in one aspect, the invention provides a method for increasing the sensitivity of a cell to a topoisomerase I inhibitor by contacting the cell with an agent that increases the level of topoisomerase I serine phosphorylation.

In another aspect, the invention provides a method for inducing cell killing, apoptosis, and/or growth arrest in a cell by contacting the cell with an agent that increases the level of topoisomerase I serine phosphorylation, and further contacting the cell with a topoisomerase I inhibitor.

In one embodiment, the agent increases the serine kinase biological activity in the cell. Preferably, the serine kinase biological activity is increased in the nucleus of the cell, the nucleolus, or in the peri-nucleolar region. Suitable agents include, for example, serine kinase agonists, activators, and cofactors. Other agents include vectors encoding a serine kinase enzyme, operably linked to a promoter. Preferably, the serine kinase phosphorylates topoisomerase I on at least one serine residue (e.g., 1, 2, 3, 4, 5, 6, 7, 8, 9, 10, or more serine residues), and wherein such phosphorylation is capable of promoting ARF-topoisomerase I complex formation. Suitable serine kinases include, for example, casein kinase II also known as protein kinase CK2 (referred to throughout this application as CKII or CK2 interchangeably), or protein kinase C (PKC).

In other embodiments, the cell is a cancer cell including, for example, a lung cancer cell, a prostate cancer cell, a hepatocellular carcinoma cell, a breast cancer cell, a colorectal cancer cell, an acute myelogenous leukemia cell, a melanoma cell, an ovarian cancer cell, a neuroendocrine carcinoma cell, a gastric cancer cell, an esophageal cancer cell, a pancreatic cancer cell, an adenocarcinoma cell, a brain cancer cell, a head and neck cancer cell, a bone marrow-derived cancer cell, a bone cancer cell, a kidney cancer cell, a retina cancer cell, a bladder cancer cell, a liver cancer cell, and a mesothelioma cancer cell. Preferably, the cell is present within a human patient.

In other embodiments, the cell is further contacted with at least one other chemotherapeutic agent. Suitable chemotherapeutic agents include, for example, alkylating agents, anti-metabolites, vinca alkaloikds, and anti-tumor antibodies.

In other embodiments, the topoisomerase I inhibitor stabilizes a topoisomerase I-DNA complex. Preferable topoisomerase I inhibitors include, for example, camptothecin, irinotecan, topotecan, and analogs thereof, for example, 9-aminocamptothecin, 9-nitrocamptothecin (Rubitecan, Oratecan, Belotecan), 10-hydroxycamptothecin, Lurtotecan, 10,11 methylenedioxycamptothecin, Morpholinocamptothecin, Extatecan, Silatecan, Diflomotecan, Homocamptotehcin, BN80927, 20-hydroxy-linked modifications to camptothecin, and others discussed in Venditto and Simanek, Mol Pharmaceutics 2010; 7(2):307-349, as well as non-camptothecin-derived topoisomerase I inhibitors that act similarly to stabilize the topoisomerase I-DNA complex as discussed in Pommier, Chemical Reviews 2009; 109:2894-2902.

In another aspect, the invention provides, for a cell expressing increased phosphorylation of topoisomerase I, a method for increasing the sensitivity of a said cell to a topoisomerase I inhibitor by contacting the cell with an agent that increases the ARF-topoisomerase I complex formation.

In another aspect, the invention provides, for a cell expressing increased phosphorylation of topoisomerase I, a method for inducing cell killing, apoptosis, and/or growth arrest in said cell by contacting the cell with an agent that increases ARF-topoisomerase I complex formation, and further contacting the cell with a topoisomerase I inhibitor.

In a related aspect, the invention provides a method for treating cancer in a patient (e.g., a human patient), who has been diagnosed as having cancer, by administering to the patient an agent that increases ARF-topoisomerase I complex formation, and further administering to the patient a topoisomerase I inhibitor In one embodiment, the agent is a vector encoding ARF, or a biologically active fragment thereof, operably linked to a promoter. Preferably, the biologically active ARF fragment contains amino acid residues 66-84 of ARF.

In another embodiment, the agent increases the amount of topoisomerase I serine phosphorylation.

In another embodiment, the agent increases the serine kinase biological activity in the cell. Preferably, the serine kinase biological activity is increased in the nucleus of the cell, the nucleolus, or in the peri-nucleolar region. Suitable agents include, for example, serine kinase agonists, activators, and cofactors. Other agents include vectors encoding a serine kinase enzyme, operably linked to a promoter. Preferably, the serine kinase phosphorylates topoisomerase I on at least one serine residue (e.g., 1, 2, 3, 4, 5, 6, 7, 8, 9, 10, or more serine residues), and wherein such phosphorylation is capable of promoting ARF-topoisomerase I complex formation. Suitable serine kinases include, for example, casein kinase II (CKII) or protein kinase C (PKC).

In other embodiments, the agent is a vector encoding ARF, or a biologically active fragment thereof, operably linked to a promoter. Preferably, the biologically active ARF fragment contains amino acid residues 66-84 of ARF.

In other embodiments, the cancer is, for example, lung cancer, prostate cancer, hepatocellular carcinoma, breast cancer, colorectal cancer, acute myelogenous leukemia, melanoma, ovarian cancer, neuroendocrine carcinoma, gastric cancer, esophageal cancer, pancreatic cancer, adenocarcinoma, adenocarcinoma, brain cancer, head and neck cancer, bone marrow-derived cancer, bone cancer, kidney cancer, retina cancer, bladder cancer, liver cancer, or mesothelioma cancer.

In other embodiments, the patient is further administered with at least one other chemotherapeutic agent including, for example, an alkylating agent, an anti-metabolite, a vinca alkaloikd, or an anti-tumor antibody. In other embodiments, the patient is administered anti-cancer radiation therapy prior to, concurrent with, or subsequent to administration of the topoisomerase I inhibitor.

Suitable topoisomerase I inhibitors stabilize the topoisomerase I-DNA complex. Preferable topoisomerase I inhibitors include, for example, camptothecin, irinotecan, topotecan, and analogs thereof, as well as non-camptothecin-derived topoisomerase I inhibitors that act similarly to stabilize the topoisomerase I-DNA complex.

As used herein, "topoisomerase I" refers to human topoisomerase I found at Gen bank accession no NM_003286 (FIG. 10).

As used herein, "p14ARF (ARF)" refers to the human ARF protein found at Genbank accession no. NP_478102 (FIG. 9) and its homologs. It is believed that ARF interacts with, and activates, topoisomerase I.

Biologically active fragments of ARF contain substantially all of the topoisomerase binding domain (i.e., amino acid residues 66-84) responsible for topoisomerase I binding. In all cases, the ARF polypeptide must be capable of binding to phosphorylated topoisomerase I. Suitable biologically active fragments include, for example, an N-terminal truncation of the ARF protein (e.g., amino acid residues 66-132), or a polypeptide fragment or chimeric protein containing substantially all of the topoisomerase I binding domain (amino acid residues 66-84).

By "serine kinase biological activity" is meant any enzymatic activity that is capable of phosphorylating a serine amino acid residue on a target protein. Typically, this is an ATP-dependent reaction in which the γ-phosphate group of an ATP molecule is transferred to the serine residue of the substrate protein. Preferred serine kinases include, for example, CKII and PKC.

By "increased serine kinase biological activity," when referring to the serine kinase biological activity within a cell in accordance with the principles of this disclosure, is meant a level of serine kinase biological activity in the cell nucleus which, following a specific treatment or intervention, is higher than would otherwise be present in the same cell absent that specific treatment or intervention (i.e., the basal level). Elevated serine kinase biological activity is preferably at least 10%, 20%, 30%, 40%, 50%, 75%, 100%, 200%, or more greater than the basal serine kinase biological activity level. Elevated serine kinase biological activity is determined using an assay which directly measures phosphorylation events attributable to the kinase activity.

A suitable assay for Protein Kinase C (PKC) can be carried out using a PKC assay kit from Upstate Biotechnology/Millipore (Temecula, Calif.). Cell lysates are prepared by lysing cells in extraction buffer (50 mM HEPES [pH 7.5], 150 mM NaCl, 0.1% Tween 20, 1 mM EDTA, 2.5 mM EGTA, 10% glycerol) that contains protease inhibitors (10 µg of aprotinin per ml, 10 µg of leupeptin per ml, 0.1 mM phenylmethylsulfonyl fluoride) and phosphatase inhibitors (1 mM NaF, 0.1 mM $Na_3VO_4$, 10 mM β-glycerophosphate) as described in Soh, et al., Molecular and Cellular Biology 1999; 19:1313-1324. 10 µg of cell lysate is then assayed in the presence of assay buffer supplied in the kit, specific PKC substrate peptide [QKRPSQRSKYL (SEQ ID NO: 1)], and γ-[$^{32}$P]-ATP (Perkin Elmer, Waltham, Mass.) for 15 minutes at 30° C., as per the instruction manual. The final reaction conditions are as follows: 3.3 mM MOPS pH 7.2, 4.2 mM β-glycerol phosphate, 0.17 mM sodium orthovanadate, 0.17 mM dithiothreitol, 0.17 mM CaCl2, 83 µM specific substrate peptide, 0.33 µM PKA inhibitor peptide, 3.3 µM compound R24571, 80 µg/ml phosphatidyl serine, 8 µg/ml, 83 µM ATP, 10 µCi γ-[$^{32}$P]-ATP. The phosphorylated substrate is then separated from residual γ-[$^{32}$P]-ATP using supplied P81 phosphocellulose paper and quantitated by scintillation counter.

A suitable assay for CKII can be carried out using a CKII assay kit from Upstate Biotechnology/Millipore (Temecula, Calif.). Cell lysates are prepared by lysing cells in extraction buffer (50 mM HEPES [pH 7.5], 150 mM NaCl, 0.1% Tween 20, 1 mM EDTA, 2.5 mM EGTA, 10% glycerol) that contains protease inhibitors (10 µg of aprotinin per ml, 10 µg of leupeptin per ml, 0.1 mM phenylmethylsulfonyl fluoride) and phosphatase inhibitors (1 mM NaF, 0.1 mM Na3VO4, 10 mM β-glycerophosphate) as described in Soh, et al., Molecular and Cellular Biology 1999; 19:1313-1324. 10 µg of cell lysate is then assayed in the presence of assay buffer supplied in the kit, specific CKII substrate peptide [RRRDDDSDDD (SEQ ID NO: 6)], and γ-[$^{32}$P]-ATP (Perkin Elmer, Waltham, Mass.) for 15 minutes at 30° C., as per the instruction manual. The final reaction conditions are as follows: 4 mM MOPS pH 7.2, 5 mM β-glycerol phosphate, 1 mM EGTA, 0.2 mM Na orthovanadate, 0.2 mM dithiothreitol, 200 µM specific substrate peptide, 0.4 mM PKA inhibitor peptide, 90 µM ATP, 10 µCi γ-[$^{32}$P]-ATP. The phosphorylated substrate is then precipitated by adding trichloracetic acid (TCA) to 10%, and quantitated by scintillation counting.

The skilled artisan recognizes that there exist a variety of kinase assays for measuring the activity of PKC, CKII, as well as other serine kinases of interest. Alternatively, serine kinase biological activity can be measured indirectly by measuring elevated levels of one or more phospho-proteins which are known to be phosphorylated by the kinase of interest. For example, as described herein, the levels of phosphorylated topoisomerase I was assessed by immunoprecipitation using an antibody that binds to both the phosphorylated and unphosphorylated form of the protein, followed by Western blotting using a phosphoserine-specific antibody. Western blots are amenable to relative quantification by densitometric analysis.

By "phosphorylates topoisomerase I", when referring to a serine kinase enzyme, is meant any serine kinase enzyme which is capable of catalyzing a phosphotransferase reaction involving the transfer of the γ-phosphate group of ATP or other nucleoside triphosphate to a serine residue of the topoisomerase I enzyme. The capability of a serine kinase (or any enzyme) to phosphorylate topoisomerase I can be determined using any kinase assay described herein or any other suitable assay known in the art for that particular kinase. A suitable kinase substrate representing the serine amino acid phosphorylating site in topoisomerase I is a polypeptide of not less than 10 amino acids, having at least one a serine residue no less than four amino acid residues from either terminus of the polypeptide, and wherein the polypeptide is identical to a portion of the human topoisomerase I enzyme (SEQ ID NO: 3).

By "topoisomerase I inhibitor" is meant a compound that is capable of inhibiting the DNA re-ligation enzymatic reaction catalyzed by topoisomerase I. Preferred topoisomerase I inhibitors are capable of creating a stabilized DNA-topoisomerase I complex sufficient to inhibit the enzymatic reaction. In order to determine whether a compound of interest is a topoisomerase I inhibitor, the relaxing of supercoiled DNA is measured in the presence of topoisomerase I and the compound of interest. The result is compared to an assay performed under the same conditions in the absence of the compound of interest, wherein a topoisomerase I inhibitor reduces or prevents relaxation of the supercoiled DNA. A suitable assay for measuring topoisomerase I inhibition is described in the Examples contained herein. Topoisomerase I inhibitors include, for example, plant alkaloids, plant alkaloid derivatives, camptothecin, irinotecan, topotecan, and analogs thereof, as well as non-camptothecin-derived topoisomerase I inhibitors that act similarly to stabilize the topoisomerase I-DNA complex.

By "stabilized complex" is meant a DNA-topoisomerase I complex in which the topoisomerase I catalytic activity has been partially or completely inhibited by the further binding of a topoisomerase I inhibitor. Normally, the DNA-topoisomerase I complex is a transient chemical intermediate species formed during the isomerase reaction. But, in the presence of a topoisomerase I inhibitor, isomerization, DNA religation, and/or DNA release is inhibited, resulting in a stabilized complex which inhibits DNA replication.

By "contacting", when referring to the interaction between a cell and an agent, is meant a physical interaction between the cell (or a cellular component) and the agent such that the desired biological effect is produced as a direct or indirect result of that interaction. Contacting may involve, for example, a physical interaction between the agent and a cell surface receptor, followed by a signal transduction event resulting in the desired biological activity within the cell. Alternatively, contacting may require internalization of the agent in order for the biological effect to be produced. Such is the case for vectors encoding serine kinase enzymes or ARF.

By a "vector" is meant a non-chromosomal nucleic acid comprising an intact replicon such that the vector may be replicated when placed within a cell, for example by a process of transformation, transfection or transduction. Vectors may be viral or non-viral. Viral vectors include retroviruses, adenoviruses, herpesvirus, papovirus, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA.

By a "promoter" is meant a nucleic acid sequence sufficient to direct transcription of a gene. Also included in the invention are those promoter elements which are sufficient to render promoter dependent gene expression controllable for cell type specific, tissue specific or inducible by external signals or agents (e.g. enhancers or repressors); such elements may be located in the 5' or 3' regions of the native gene, or within an intron.

By "operably linked" is meant that a nucleic acid molecule and one or more regulatory sequences (e.g., a promoter) are connected in such a way as to permit expression and/or secretion of the product (e.g., a protein) of the nucleic acid molecule when the appropriate molecules (e.g., transcriptional activator proteins) are bound to the regulatory sequences.

In another aspect, the invention provides a method for inducing apoptosis, cell killing, and/or growth arrest in a cell by contacting the cell with an agent that inhibits the binding of ARF to topoisomerase I. The binding may be inhibited by an antibody or other binding agent (e.g. a peptide, an aptamer, or a peptidomimetic) which disrupts the interaction between ARF to topoisomerase I. The agent may bind directly to ARF or to topoisomerase I and may competitively or non-competitively inhibit the ARF-topoisomerase I binding interaction. Suitable antibodies include, for example, ARF-specific antibodies and topoisomerase I-specific antibodies. Alternatively, a phosphatase that dephosphorylates topoisomerase I may be used to reduce ARF binding to topoisomerase I. A CK2 inhibitor such as TBB (4,5,6,7-tetrabromobenzotriazole) could also be used to reduce CK2-mediated phosphorylation of topoisomerase I. In preferred embodiments, the method disrupts existing ARF-topoisomerase I complexes. In other embodiments, ARF binding to HDM2 is increased. In other embodiments, p53 biological activity is increased.

In another aspect, the invention provides methods for determining the sensitivity of a cancer cell to a topoisomerase I inhibitor comprising: (i) determining the nuclear localization of ARF within the cancer cell, and (ii) identifying the cancer cell as being sensitive to a topoisomerase I inhibitor when the ARF is substantially localized to the nucleolus and identifying a cancer cell as being resistant to a topoisomerase I inhibitor when said ARF is substantially disbursed in the nucleus of said cell. In this context, the term "substantially" means greater than 50%. In preferred embodiments in which cancer cells are identified as being sensitive to a topoisomerase inhibitor, more than 50%, 60%, 70%, 80%, 90%, 95%, or 99% of the ARF is present the nucleolus or the nucleolus and perinucleolar region.

In another aspect, the invention provides methods for determining the sensitivity of a cancer cell to a topoisomerase I inhibitor comprising: (i) determining the ratio of free ARF to ARF bound to topoisomerase I in the nucleus of the cancer cell, and (ii) identifying the cancer cell as being sensitive to a topoisomerase I inhibitor when the ratio is less than 1, and identifying a cancer cell as being resistant to a topoisomerase I inhibitor when the ratio is greater than 1. In preferred embodiments in which cancer cells are identified as being sensitive to a topoisomerase inhibitor, the ratio is less than 0.9, 0.8, 0.7, 0.6, 0.5, 0.4, 0.3, 0.2, or 0.1. In preferred embodiments in which cancer cells are identified as being resistant to a topoisomerase inhibitor, the ratio is greater than 2, 3, 4, 5, 7, 10, 20, 25, 50, 90, or 100.

In another aspect, the invention provides methods for determining the sensitivity of a cancer cell to a topoisomerase I inhibitor comprising: (i) determining the ratio of unphosphorylated topoisomerase I to phosphorylated topoisomerase I in the nucleus of the cancer cell, and (ii) identifying the cancer cell as being sensitive to a topoisomerase I inhibitor when the ratio is less than 1, and identifying a cancer cell as being resistant to a topoisomerase I inhibitor when the ratio is greater than 1. In preferred embodiments in which cancer cells are identified as being sensitive to a topoisomerase inhibitor, the ratio is less than 0.9, 0.8, 0.7, 0.6, 0.5, 0.4, 0.3, 0.2, or 0.1. In preferred embodiments in which cancer cells are identified as being resistant to a topoisomerase inhibitor, the ratio is greater than 2, 3, 4, 5, 7, 10, 20, 25, 50, 90, or 100.

In preferred embodiments of the aspects of this invention, the topoisomerase inhibitor is camptothecin, irinotecan, or topotecan. In other embodiments, the cancer cell is a lung cancer cell, prostate cancer cell, hepatocellular carcinoma cell, breast cancer cell, colorectal cancer cell, acute myelogenous leukemia cell, melanoma cell, or adenocarcinoma cell, ovarian cancer cell, neuroendocrine carcinoma cell, gastric cancer cell, esophageal cancer cell, pancreatic cancer, adenocarcinoma, brain cancer, head and neck cancer, bone marrow-derived cancer, bone cancer, kidney cancer, retina cancer, bladder cancer, liver cancer, or mesothelioma cancer.

In another aspect, the invention provides kits for determining the sensitivity of a cell (e.g., a cancer cell) to a topoisomerase I inhibitor. An exemplary kit may comprise (i) an anti-phosphoserine antibody specific for a serine phosphorylated epitope on topoisomerase I, and (ii) an anti-topoisomerase I antibody. The kit may also include (iii) an anti-ARF antibody. In a preferred embodiment, the anti-topoisomerase I antibody binds to human topoisomerase I. In another preferred embodiment, the anti-ARF antibody binds to human ARF.

In another aspect, the invention provides a cell containing a recombinant vector and a topoisomerase I inhibitor. Suitable recombinant vectors include vectors encoding a serine kinase (e.g., CKII or PKC), ARF, or a biologically active fragment of ARF. In preferred embodiments, the cell further contains a stabilized DNA-topoisomerase I complex.

In another aspect, the invention provides a cell comprising a topoisomerase I inhibitor and further expressing an elevated serine kinase biological activity, wherein the cell has been contacted with an agent that elevates the serine kinase biological activity relative to the serine kinase biological activity in the same cell which has not been contacted with the agent.

In another aspect, the invention provides methods for determining the sensitivity of a cancer cell to a topoisomerase I inhibitor, comprising: (i) determining status of phosphorylation on serine 506 amino acid residue of topoisomerase I within the cancer cell by way of an assay; and (ii) identifying the cancer cell as being sensitive to the topoisomerase I inhibitor when phosphorylation of serine 506 amino acid residue of topoisomerase I is above a predetermined threshold as determined by the assay, and identifying said cancer cell as being resistant to the topoisomerase I inhibitor when phosphorylation of serine 506 amino acid residue of topoisomerase I is below the predetermined threshold as determined by the assay. In preferred embodiments, the predetermined threshold is a ratio of unphosphorylated topoisomerase I to phosphorylated topoisomerase I within said cancer cell. In some embodiment, CKII RNA expression of the cancer cell can be evaluated as a confirmatory or supportive diagnostic test.

In preferred embodiments of the aspects of this invention, the presence or absence of phosphorylation on serine 506 amino acid residue of topoisomerase I is determined by an antibody based assay, which may include an antibody that binds phosphorylated serine 506 amino acid residue of topoisomerase I, but does not bind nonphosphorylated serine 506 amino acid residue of topoisomerase I, and or include an antibody that binds unphosphorylated serine 506 amino acid residue of topoisomerase I, but does not bind phosphorylated serine 506 amino acid residue of topoisomerase I. In some embodiments the antibody may be a monoclonal antibody, and in some embodiments the antibody may be a polyclonal antibody.

In another aspect, the invention provides methods for treating cancer in a patient, comprising: (i) determining status of phosphorylation, by way of an assay, on serine 506 amino acid residue of topoisomerase I in a biological specimen from the patient; (ii) identifying the patient as being sensitive to a topoisomerase I inhibitor when phosphorylation of serine 506 amino acid residue of topoisomerase I is above a predetermined threshold as determined by the assay; and (iii) administering the topoisomerase I inhibitor to the patient. In some embodiments, the biological specimen may be tumor cells, tumor tissue, blood, urine, and/or sputum.

In another aspect, the invention provides methods of increasing the sensitivity of a cancer patient to a topoisomerase inhibitor, comprising administering a CKII activator to the cancer patient in an amount sufficient to decrease ratio of unphosphorylated topoisomerase I to phosphorylated topoisomerase I. In some embodiments, the CKII activator is 1-ethyl-4,5-dicarbamoylimidazole.

BRIEF DESCRIPTION OF THE DRAWINGS

FIG. 1 is a series of electrophoretic gel separations of nuclear proteins from DU145, H358, and H23 cells. FIG. 1A is a silver-stained electrophoretic gel showing cellular proteins corresponding in size to topoisomerase I that bound to an immobilized fusion protein composed of the N-terminal portion of ARF (ARF-N-term; exon 1β, amino acid residues 1-64) and the full-length ARF protein. FIG. 1B shows a Western analysis of topoisomerase I that bound to immobilized full length ARF or Nickel-NTA agarose lacking immobilized fusion protein (control, middle panel). FIG. 1C shows co-binding of topoisomerase I and ARF following immunoprecipitation of H358 and H23 nuclear extracts with an anti-topo I antibody followed by Western detection of topo I or ARF in the immunoprecipitated material, before (left panel) or 48 hours after treatment with Adp14 (replication-defective adenoviral vector encoding full length ARF), moi=20 pfu/cell (middle panel). Far right panel shows material that remained unbound by the anti-topo I antibody.

FIG. 3C also shows that HT29 cells have low levels of topo I serine phosphorylation and ARF-topoisomerase I complexation relative to H358 cells. This data demonstrates that the ARF-topoisomerase I complex formation is a phosphorylation dependent event.

FIG. 4A is an electrophoretic gel separation and Western of topoisomerase I and ARF following subcellular fractionation. These data show that topoisomerase I is concentrated in the nucleolus of both H538 and H23 cells, and ARF is also concentrated in the nucleolus of H538 cells. By contrast, ARF has is distributed approximately evenly between the nucleolus and the nucleoplasm of H23 cells. FIG. 4B is a series of photomicrographs showing the immunofluorescence pattern of ARF in fixed and permeabilized H358 and H23 cells. This confirms the findings of FIG. 4A and demonstrates that there is reduced nucleolar ARF localization in H23 cells. FIG. 4C is an electrophoretic separation following co-immunoprecipitation analysis of Nucleophosmin (NPM/B23) and ARF in H358 and H23 nuclear extracts.

FIG. 5D (upper panel shows topoisomerase I immunoprecipitation followed by topoisomerase I or ARF Western following various treatments. Lanes correspond to the same treatments as in FIG. 5A. Digital analyses of ARF band intensities are shown below the ARF lanes. FIG. 5D (middle panel) is an ethidium bromide-stained agarose gel of the reaction products of an in vitro topoisomerase I assay measuring loss of supercoiled plasmid DNA in the presence of 0.06 μg H358 nuclear extract (amount that converts 50% of supercoiled plasmid to relaxed form; see FIG. 2A). Numbered lanes correspond to the same treatments as in FIG. 5A. s=supercoiled; r=relaxed form. FIG. 5D (lower panel) is a graphical representation of the relative supercoil band intensities of lanes 1-5 of the ethidium bromide-stained agarose gel shown in the middle panel. These data demonstrate that ARF-topoisomerase I complex formation and topoisomerase I activity were altered in a predictable and coordinate manner by overexpressing or inhibiting ARF.

FIGS. 7A-C show the relative amounts of (A) serine phosphorylation of topoisomerase I, (B) total topoisomerase I, and (C) ARF-topoisomerase I complex following topoisomerase I immunoprecipitation in the indicated cell types. FIG. 7D is a graph showing the viability of the indicated cell types 3 days after treatment with camptothecin.

FIG. 9 is the amino acid sequence of human ARF, as provided in accession no. NP_478102 (SEQ ID NO: 2).

FIG. 10 is the amino acid sequence of human topoisomerase I, as provided in accession no NM_003286. (SEQ ID NO: 3).

FIG. 11A shows a graph of 3-day viability assays carried out in 96 well plates. FIG. 11B1-B3 show bar graphs of PKC, CK2, and cdk1 enzyme levels and Western blots of PKC, CK2, and cdk1 protein levels in cancer cell lines. Western blots of actin levels serves as a control. FIG. 11C1-C3 show bar graphs and Western blots of PKC, CK2, and cdk1 activities and protein levels, respectively, in normal cell lines, compared to H358 and H23. FIG. 11D shows topo-I immunoprecipitation followed by topo-I Western (top row) or phosphoserine Western (bottom row).

DETAILED DESCRIPTION OF INVENTION

Figure 2:
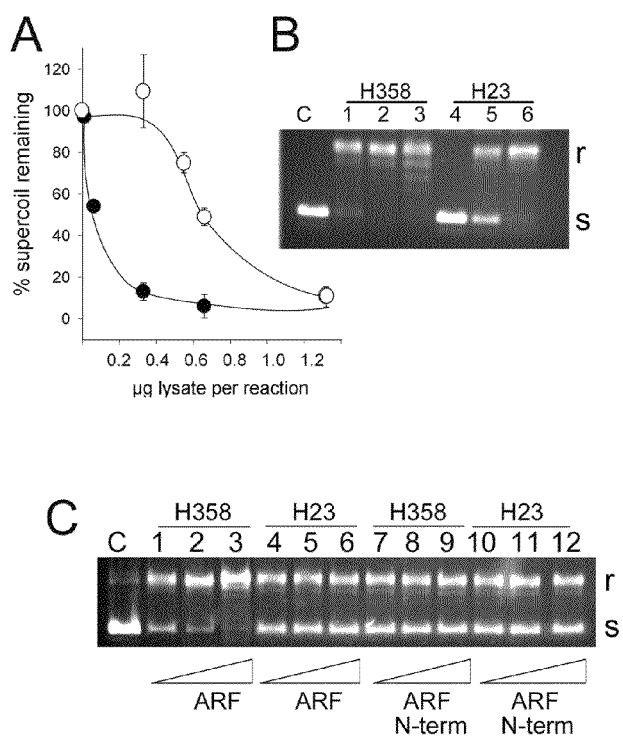
FIG. 2A is a graph showing that nuclear extracts from H358 cells (closed circles) have greater topoisomerase I activity compared to and H23 cells (open circles) in an in vitro assay measuring the conversion of supercoiled plasmid DNA ("s") to the relaxed form ("r").
FIG. 2B is an agarose gel electrophoresis of reaction products of a typical in vitro topoisomerase I assay in which 0.32, 0.65, or 1.3 μg of H358 extract (lanes 1-3, respectively) or H23 extract (lanes 4-6, respectively) were added per reaction. Lane "C" (control) shows migration of supercoiled plasmid in the absence of cell extract.
FIG. 2C is an agarose gel electrophoresis showing that addition of purified ARF bacterial fusion protein in the topoisomerase activity assay increases the topoisomerase I activity of H358 nuclear extracts (lanes 1-3), but not H23 nuclear extracts (lanes 4-6). The purified ARF-N-term bacterial fusion protein, which retains only the N-terminal 64 amino acid residues of ARF (lanes 7-12) had no effect on topoisomerase I activity.

The present inventions are based on different mechanisms for inducing cell death, apoptosis and/or growth arrest in cancer cells. Each mechanism is based upon altering (i.e., increasing or decreasing) the amount of ARF-topoisomerase I complex formation. One mechanism is based on the discovery that reduced topoisomerase I serine phosphorylation and/or ARF-topoisomerase I complex formation renders cells less sensitive (or insensitive) to the apoptotic and/or growth arresting effects of topoisomerase I inhibitors. Sensitivity to topoisomerase I inhibitors may be restored by increasing amount of ARF-topoisomerase I complex formation which may be done by increasing the serine phosphorylation of the enzyme (e.g., using CKII or PKC), and/or by increasing ARF in order to promote complex formation. Another mechanism is based on the discovery that disruption of ARF-topoisomerase I complex formation correlates with cell death, apoptosis and/or growth arrest.

As described in more detail in the following examples, analysis of the H23 non-small cell cancer cell line identified cancer-related defects in topoisomerase I-ARF binding. Specifically, the loss of topoisomerase I serine phosphorylation caused a corresponding loss of topoisomerase I activity. Additionally, the absence of topoisomerase I serine phosphorylation resulted in reduced ARF binding and caused an aberrant nuclear distribution of ARF. It was further observed in H23 cells that only about half of the cellular ARF was bound to NPM, a nucleolar protein. Normally, virtually all cellular ARF is NPM-bound.

Increased ARF-Topoisomerase I Complex Formation Increases Sensitivity to Topoisomerase I Inhibitors.

The mechanisms that regulate topoisomerase I activity are of considerable therapeutic interest, since topoisomerase I has proven to be an important target for chemotherapy (Pommier, et al., Biochim Biophys Acta 1998; 1400(1-3):83-105; Liu, L. F., Annu Rev Biochem 1989; 58:351-75). A potent class of chemotherapeutic drugs that target topoisomerase I are derived from the plant alkaloid, camptothecin, a group that includes irinotecan (Camptosar) and Topotecan. These agents have been highly effective for the treatment of a variety of solid tumors that have shown resistance to other treatments, including non-small cell lung cancer (Rothenberg, M. L., Oncologist 2001; 6(1):66-80). Camptothecin and its derivatives prevent the re-ligation of the cleavable complex, a topoisomerase I reaction intermediate, thereby creating lethal topoisomerase I-induced DNA strand breaks (Champoux, J., Annu Rev Biochem 2001; 70:369-413). In addition, several non-camptothecin-derived topoisomerase I inhibitors that act through a similar mechanism are being developed and evaluated (Pommier, Chemical Reviews 2009; 109:2894-2902). As with many chemotherapeutic treatments, however, de novo or acquired resistance to camptothecins is common, and can occur through a variety of mechanisms (Rasheed, et al., Oncogene 2003; 22(47):7296-304; Xu, et al., Ann Oncol 2002; 13(12):1841-51), including downregulation of topoisomerase I activity (Pommier, et al., Ann NY Acad Sci 1996; 803:60-73).

Figure 5:
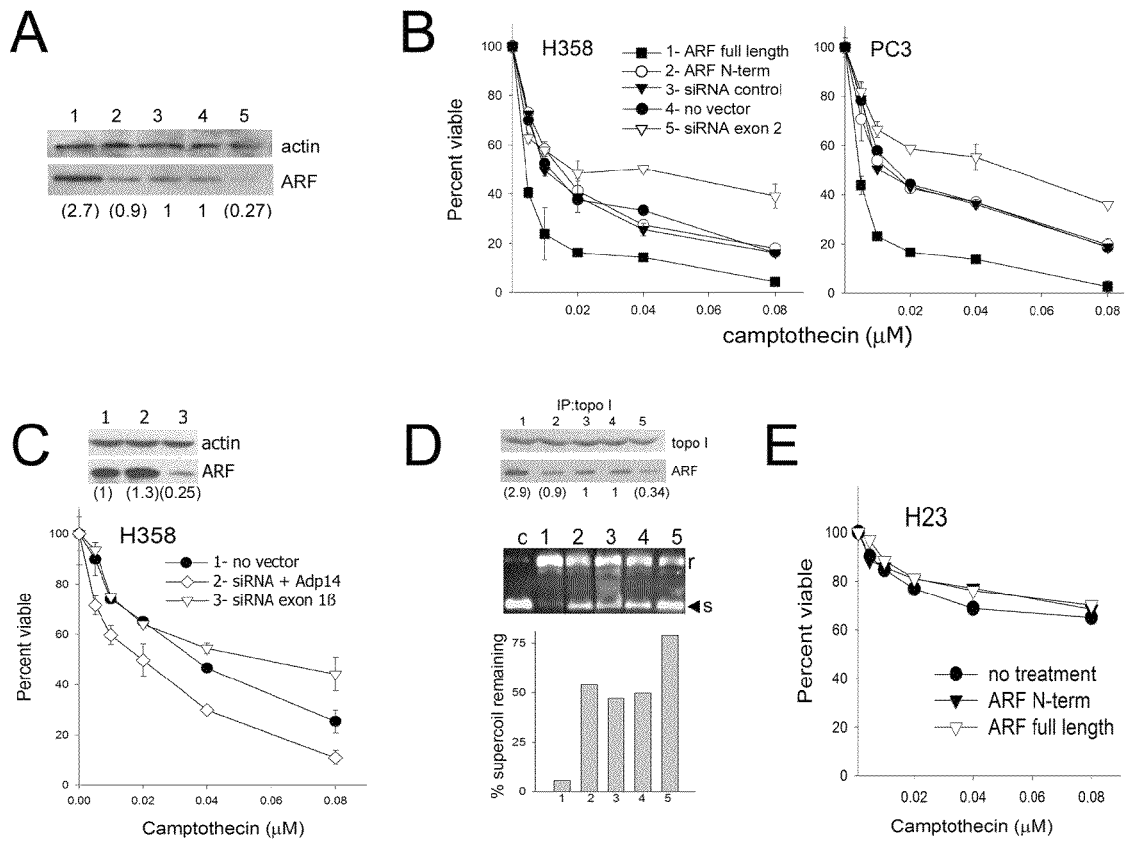
FIG. 5A is an electrophoretic separation and Western analysis of H358 cellular actin (top row) or ARF (bottom row) 48 hours after treatment with Adp14 (replication-defective adenoviral vector encoding full-length ARF) (lane 1) or Ad1β (replication-defective adenoviral vector encoding the N-terminal 64 amino acid residues of ARF encoding by the first exon (exon 1β of ARF) (lane 2), or 72 hours after treatment with siRNA control sequence (lane 3), or ARF siRNA to exon 2 (lane 5). Lane 4 shows actin and ARF levels in untreated H358 cells. Digital analyses of ARF band intensities are shown beneath the ARF Western blot.
FIG. 5B is a series of graphs showing H358 and PC-3 cell viabilities assayed 5 days post-vector treatment (adenoviral vector, moi 20 pfu/cell, or siRNA), and 4 days post treatment with increasing doses of camptothecin. Viability is expressed as a percent of no-camptothecin control for each vector or siRNA treatment. Results represent average of triplicate wells, with standard deviations indicated. Treatments: Adp14 (ARF full length ■); Ad1β (ARF N-term ○); siRNA control (▼); no vector (●); siRNA exon 2 (∇).
FIG. 5C shows the results of a Western analysis (top panel) of H23 cellular actin and ARF levels in untreated cells (lane 1) or 72 hours after treatment with ARF siRNA to exon 1β (lane 3), or siRNA plus Adp14 (moi=100) (lane 2). Digital analyses of ARF levels are shown below ARF lanes. (lower panel) H358 cell viability assay following the indicated treatments. Viability was measured 3 days post-start of camptothecin treatment. Together, these data demonstrate that reduced ARF levels, and thus reduced ARF-topoisomerase I complex formation (see FIG. 5D), renders cells less sensitive to topoisomerase I inhibitors.
FIG. 5D shows ARF-topoisomerase I complex formation in H358 cells following various treatments, and correlates differences in complex formation with differences in topoisomerase I activity.
FIG. 5E is a graph showing the H23 cell viability assay performed as described above. Consistent with the observation that topoisomerase I activity in H23 cells is not enhanced by ARF overexpression, this experiment demonstrates that ARF overexpression does not render H23 cells sensitive to topoisomerase I inhibitors.

The following examples demonstrate that reduced levels of topoisomerase I activity and failure of ARF/topoisomerase I complex formation in H23 cells correlates with camptothecin resistance, while ectopic over expression of ARF and increased ARF/topoisomerase I complex formation in H358 cells results in enhanced camptothecin sensitivity (FIG. 5).

Without wishing to be bound by any theory, it is believed that the apoptosis, cell killing and/or growth arrest caused by topoisomerase I inhibitors requires a catalytically active topoisomerase I enzyme. Catalytic activity is enhanced by ARF-topoisomerase I complex formation, which itself requires serine phosphorylation of the enzyme. Thus, the following examples demonstrate that ARF-topoisomerase I complex formation can be increased by increasing the amount of serine phosphorylation of the enzyme and/or increasing the amount of ARF (or a biologically active fragment of ARF) available for topoisomerase I binding. The resulting elevation in ARF-topoisomerase I complex formation increases the sensitivity of the cell to topoisomerase I inhibitors which bind to, and stabilize, the covalent complex formed as an intermediate during the isomerase reaction. The stabilized complexes likely prevent further DNA replication.

Disruption of ARF-Topoisomerase I Complex Formation Induces Apoptosis and/or Growth Arrest in Cancer Cells.

ARF is a well known positive regulator of the p53 tumor suppressor. ARF interacts with and sequesters human double minute (HDM2) or its equivalent, a negative regulator of p53. In doing so, ARF promotes the accumulation of p53 protein which results in p53-mediated cell cycle arrest or apoptosis.

As demonstrated herein, ARF is normally localized to the nucleolus as a result of its topoisomerase I binding. This effectively prevents ARF from binding to HDM2, thereby permitting HDM2-inhibition of p53. However, disruption of the ARF-topoisomerase I binding interaction allows ARF to redistribute from the nucleolus to the nucleoplasm (FIG. 4). Without wishing to be bound by any theory, it is believed that this redistribution allows ARF to bind and sequester HDM2, causing a dis-inhibition or an activation of p53. It is this p53 activation which underlies the apoptotic and growth arresting effect caused by the disruption of ARF-topoisomerase I complex formation.

Vectors Suitable for Delivery to Humans

This invention features methods and compositions for treating cancer. The cancer may be treated by inducing cell death (e.g., apoptosis) or growth arrest in the cancer cells. In one aspect, the invention features methods of gene therapy to express ARF or a serine kinase (e.g., CKII or PKC) in the cancer cells of a patient. Gene therapy, including the use of viral vectors as described herein, seeks to transfer new genetic material (e.g., polynucleotides encoding a serine kinase) to the cells of a patient with resulting therapeutic benefit to the patient. For in vivo gene therapy, expression vectors encoding the gene of interest is administered directly to the patient. The vectors are taken up by the target cells and the serine kinase gene expressed. Several recent reviews are available discussing methods and compositions for use in gene therapy (Eck et al., in Goodman & Gilman's The Pharmacological Basis of Therapeutics, Ninth Edition, Hardman et al., eds., McGray-Hill, New York, 1996, Chapter 5, pp. 77-101; Wilson, Clin. Exp. Immunol. 107 (Suppl. 1):31-32, 1997; Wivel et al., Hematology/Oncology Clinics of North America, Gene Therapy, S. L. Eck, ed., 12(3):483-501, 1998; Romano et al., Stem Cells, 18:19-39, 2000, U.S. Pat. No. 6,080,728).

Adenoviruses are able to transfect a wide variety of cell types, including non-dividing cells. There are more than 50 serotypes of adenoviruses that are known in the art, but the most commonly used serotypes for gene therapy are type 2 and type 5. Typically, these viruses are replication-defective; genetically modified to prevent unintended spread of the virus. This is normally achieved through the deletion of the E1 region, deletion of the E1 region along with deletion of either the E2 or E4 region, or deletion of the entire adenovirus genome except the cis-acting inverted terminal repeats and a packaging signal (Gardlik et al., Med. Sci. Monit. 11: RAI 10-121, 2005).

Retroviruses are also useful as gene therapy vectors and usually (with the exception of lentiviruses) are not capable of transfecting non-dividing cells. The invention includes use of any appropriate type of retrovirus that is known in the art, including, but not limited to, HIV, SIV, FIV, EIAV, and Moloney Murine Leukaemia Virus (MoMLV). Typically, therapeutically useful retroviruses including deletions of the gag, pol, or env genes.

Adeno-associated virus (AAV) vectors can achieve latent infection of a broad range of cell types, exhibiting the desired characteristic of persistent expression of a therapeutic gene in a patient. The invention includes the use of any appropriate type of adeno-associated virus known in the art including, but not limited to AAV1, AAV2, AAV3, AAV4, AAV5, and AAV6 (Lee et al., Biochem J. 387: 1-15, 2005; U.S. Patent Publication 2006/0204519).

Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In vivo DNA-mediated gene transfer into a variety of different target sites has been studied extensively. Naked DNA may be administered using an injection, a gene gun, or electroporation. Naked DNA can provide long-term expression in muscle (Wolff, et al., Human Mol. Genet., 1:363-369, 1992; Wolff, et al., Science, 247, 1465-1468, 1990). DNA-mediated gene transfer has also been characterized in liver, heart, lung, brain and endothelial cells (Zhu, et al., Science, 261: 209-211, 1993; Nabel, et al., Science, 244: 1342-1344, 1989). DNA for gene transfer also may be used in association with various cationic lipids, polycations and other conjugating substances (Przybylska et al., J. Gene Med., 6: 85-92, 2004; Svahn, et al., J. Gene Med., 6: S36-S44, 2004).

Methods of gene therapy using cationic liposomes are also well known in the art. Exemplary cationic liposomes for use in this invention are DOTMA, DOPE, DOSPA, DOTAP, DC-Chol, Lipid GL-67™, and EDMPC. These liposomes may be used to encapsulate a serine kinase vector for delivery into target cells.

Typically, vectors made in accordance with the principles of this disclosure will contain promoters that will cause constitutive expression of the serine kinase coding sequence, although inducible promoters may be used.

Administration of Topoisomerase I Inhibitors

In addition to elevating the serine kinase levels (e.g., CKII and PKC levels) in a cancer cell, sufficient to increase phosphorylation of topoisomerase I, or increasing ARF levels sufficient to enhance the formation of an ARF/topoisomerase I complex it is desirable that the cancer cells be further contacted with one or more topoisomerase I inhibitors. Typically, patients diagnosed as having cancer will be administered a pharmaceutical formulation containing a topoisomerase I inhibitor. Suitable topoisomerase I inhibitors include, for example, camptothecin, irinotecan, topotecan, and analogs of these inhibitors, as well as non-camptothecin-derived topoisomerase I inhibitors that act similarly to stabilize the topoisomerase I-DNA complex. The administration of topoisomerase I inhibitors may be by any suitable means that results in an anti-neoplastic effect. The topoisomerase I inhibitor may be administered in any appropriate amount, in any suitable carrier substance, and is generally present in an amount of 1-95% by weight of the total weight of the composition. The composition may be provided in a dosage form that is suitable for the oral, parenteral (e.g., intravenously, intramuscularly), rectal, or transdermal administration. Thus, the composition may be in form of, e.g., tablets, capsules, pills, powders, granulates, suspensions, emulsions, solutions, gels including hydrogels, pastes, ointments, creams, suppositories, enemas, or injectables. The pharmaceutical compositions may be formulated according to conventional pharmaceutical practice (see, e.g., Remington: The Science and Practice of Pharmacy, (19th ed.) ed. A. R. Gennaro, 1995, Mack Publishing Company, Easton, Pa. and Encyclopedia of Pharmaceutical Technology, eds. J. Swarbrick and J. C. Boylan, 1988 1999, Marcel Dekker, New York.

Camptothecin, irinotecan, topotecan and their analogs, for example, may be administered at doses of about 0.1-1000 mg/kg/day (e.g., about 1, 10, 25, 50, 75, 100, 250, 500, 750, or 1000 mg/kg/day) (U.S. Pat. Nos. 5,004,758, 5,340,817, 5,633,016, 5,859,022, 5,910,491, 6,040,306, 6,214,821, 6,534,080; hereby incorporated by reference), or over the recommended dose rage of 50 to 350 mg/m$^2$ to patients, in accordance with dosing schedules recommended by the drug manufacturer. Administration of any of the topoisomerase I inhibitors described herein may continue for about a week, a month, six months, a year, or even the lifetime of the patient.

Protein Kinase CK2 as a Central Regulator of Topoisomerase I Hyperphosphorylation and Activity and Cellular Sensitivity to Camptothecin.

Experimental inhibition or activation of CK2 demonstrates that CK2 is necessary and sufficient for regulating these properties of topoisomerase I and for altering cancer cell responses to camptothecin. The results establish a cause and effect relationship between CK2 activation and camptothecin sensitivity. Biomarkers based on CK2, topoisomerase I phosphorylation, or topoisomerase I/p14ARF complex formation can provide diagnostic indicators of therapy responsive tumors.

The present inventors have reported on two non small cell lung cancer cell lines, H358 and H23, that express similar levels of topo I protein but have high and low sensitivity to camptothecin, respectively, that correlates with high or low levels of topo I serine phosphorylation and topo I activity (Bandyopadhyay, et. al., Biochemistry 2007; 46:14325-14334). They have also found that the underphosphorylated and less active form of topo I in H23 cells can be activated by CK2 treatment in vitro, further suggesting that CK2 could be a factor in vivo in regulating camptothecin sensitivity in cells. Taken together, these observations suggest that one or more topo I serine phosphorylating activities could have a general role in a variety of cancers to regulate topo I activity in vivo in ways that affect the cellular response to camptothecin-related drugs.

As demonstrated herein, CK2 is frequently upregulated in cancer cell lines, and that levels of CK2, unlike PKC and cdk-1, display consistent correlation with the appearance of hyperphosphorylated topo I and with increased cellular sensitivity to camptothecin. Furthermore, experimental modulation of cellular CK2 activity demonstrate a functional relationship between CK2 overexpression, topo I hyperphosphorylation, and cellular sensitivity to camptothecin. These results identify CK2 as a frequent and central regulator of cellular sensitivity to camptothecin in cancer cell lines. Thus, biomarkers based on CK2, topoisomerase I phosphorylation, or topoisomerase I/p14ARF complex formation can provide diagnostic indicators of therapy responsive tumors.

Camptothecin Sensitivity of Normal and Cancer-Derived Cell Lines Correlates with Topo I Phosphorylation and CK2 Activity but not PKC or cdk1 Activity.

Figure 11:
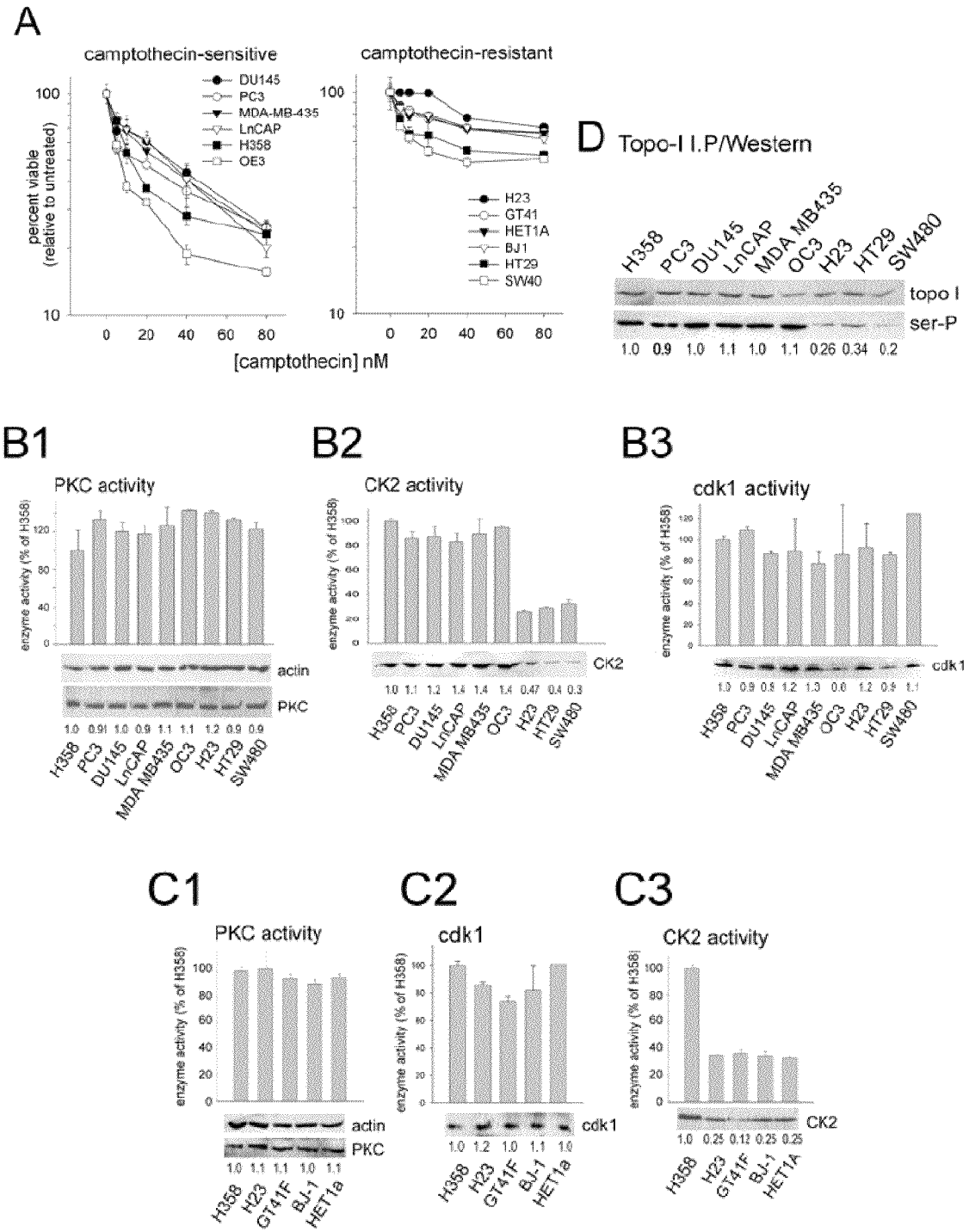

Cell lines with overexpressed CK2 (FIGS. 11B1-B3 and 11C1-C3) display hyper serine phosphorylation of topo I (FIG. 11D) that correlate with sensitivity to camptothecin (FIG. 1A). The cellular levels of two other serine kinases, PKC and cycline-dependent kinase 1(cdk1), both of which have been implicated in topo I serine phosphorylation, do not correlate with sensitivity to camptothecin (FIG. 11A-C3).

Figure 12:
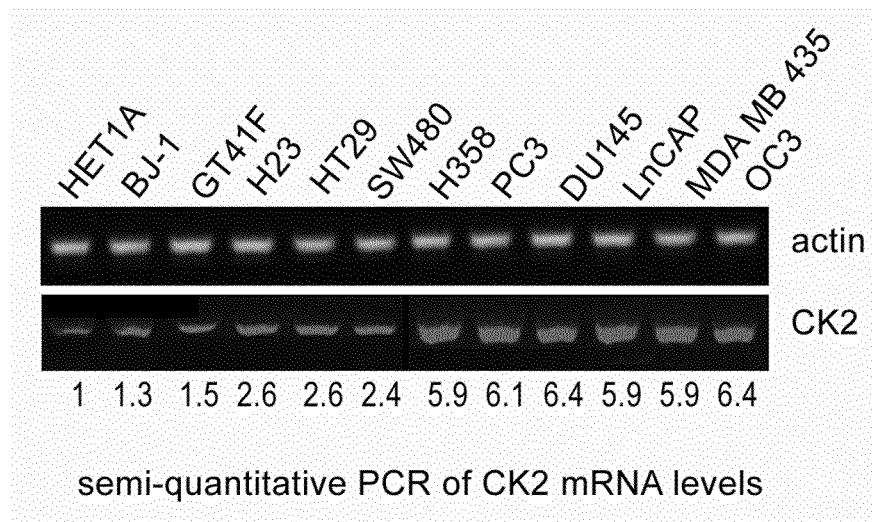
FIG. 12 shows the result of a semi quantitative PCR of CK2 mRNA levels. Analysis of CK2 mRNA levels in cellular RNA, normalized to levels in HET1A cells, showed that levels in normal cells (HET1A, BJ-1, GT41F) and the 3 camptothecin-resistant cancer cell lines (H23, HT29, SW480) are lower than levels in the 6 camptothecin-sensitive cancer cell lines (H358, PC3, DU145, LnCAP, MDAMB-435, OC3). Digital quantitation of band intensities for CK2 are shown below the lanes.

Furthermore, camptothecin sensitivity of normal and cancer-derived cell lines correlate with CK2 mRNA levels, indicating that a PCR-based assay to measure CK2 mRNA levels can be used clinically to identify tumors responsive to camptothecin and related drugs. As shown in FIG. 12, a semiquantitative RT-PCR analysis of CK2 mRNA levels in cellular RNA, normalized to levels in HET1 A cells, showed that levels in normal cells (HET1A, BJ-1, GT41F) and the 3 camptothecin-resistant cancer cell lines (H23, HT29, SW480) are lower than levels in the 6 camptothecin-sensitive cancer cell lines (H358, PC3, DU145, LnCAP, MDAMB-435, OC3).

Figure 13:
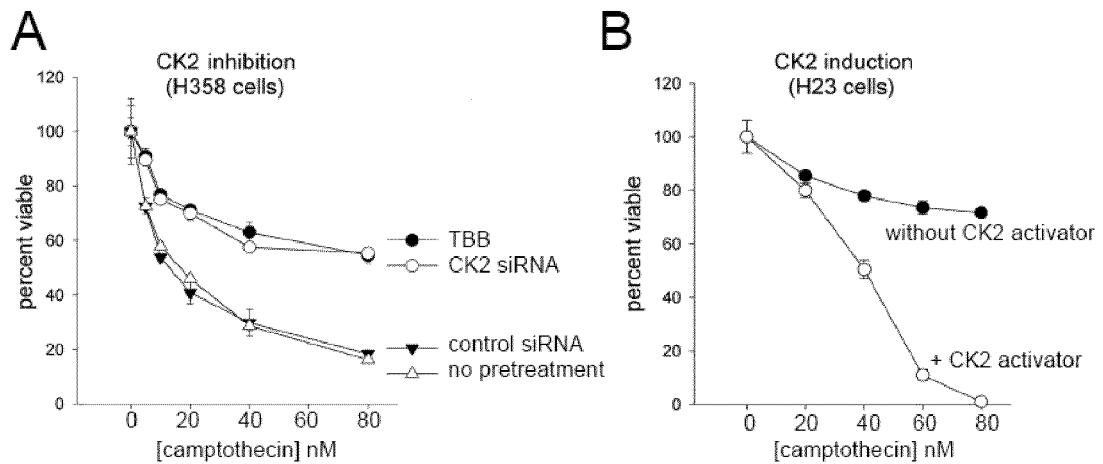
FIG. 13A shows a graph of 3-day viability assay of camptothecin-sensitive H358 lung cancer cells, pretreated with the CK2 inhibitor, 4,5,6,7-tetrabromobenzotriazole (TBB) (10 μM, 1 hr) or transfected with CK2 siRNA, or control, scrambled sequence siRNA, followed immediately by treatment with increasing doses of camptothecin for 18 hours. Control cells received no pretreatment.
FIG. 13B shows a graph of 3-day viability assay of camptothecin-resistant H23 cells, treated for 18 hours with increasing doses of camptothecin, in the presence or absence of the CK2 activator, 1-ethyl-4,5-dicarbamoylimidazole. CK2 activator treatment was for the duration of the assay. Cell viability was scored 3 days post-start of camptothecin treatment.

In addition, a functional relationship has been established between CK2 and the cellular response to camptothecin (FIGS. 13A and B), further validating CK2 as a biomarker for therapy responsiveness. Experimental inhibition of CK2 in camptothecin-sensitive H358 cells makes these cells more resistant to camptothecin (FIG. 13A), and conversely, experimental activation of CK2 in camptothecin-resistant H23 cells makes them more sensitive to camptothecin (FIG. 13B). These experiments show that CK2 is necessary and sufficient for inducing the hyperphosphorylation and activation of topo I that leads to increase cellular sensitivity to camptothecin.

Novel Topoisomerase I Phospho Epitope Identifies Camptothecin-Sensitive Cancer Cell Lines.

A novel CK2-mediated phosphorylation site on serine position 506 of topo I has been identified, which correlates with tumor cell sensitivity to camptothecin, a topo I drug from which a potent class of chemotherapeutic agents have been derived, including irinotecan and topotecan.

Figure 14:
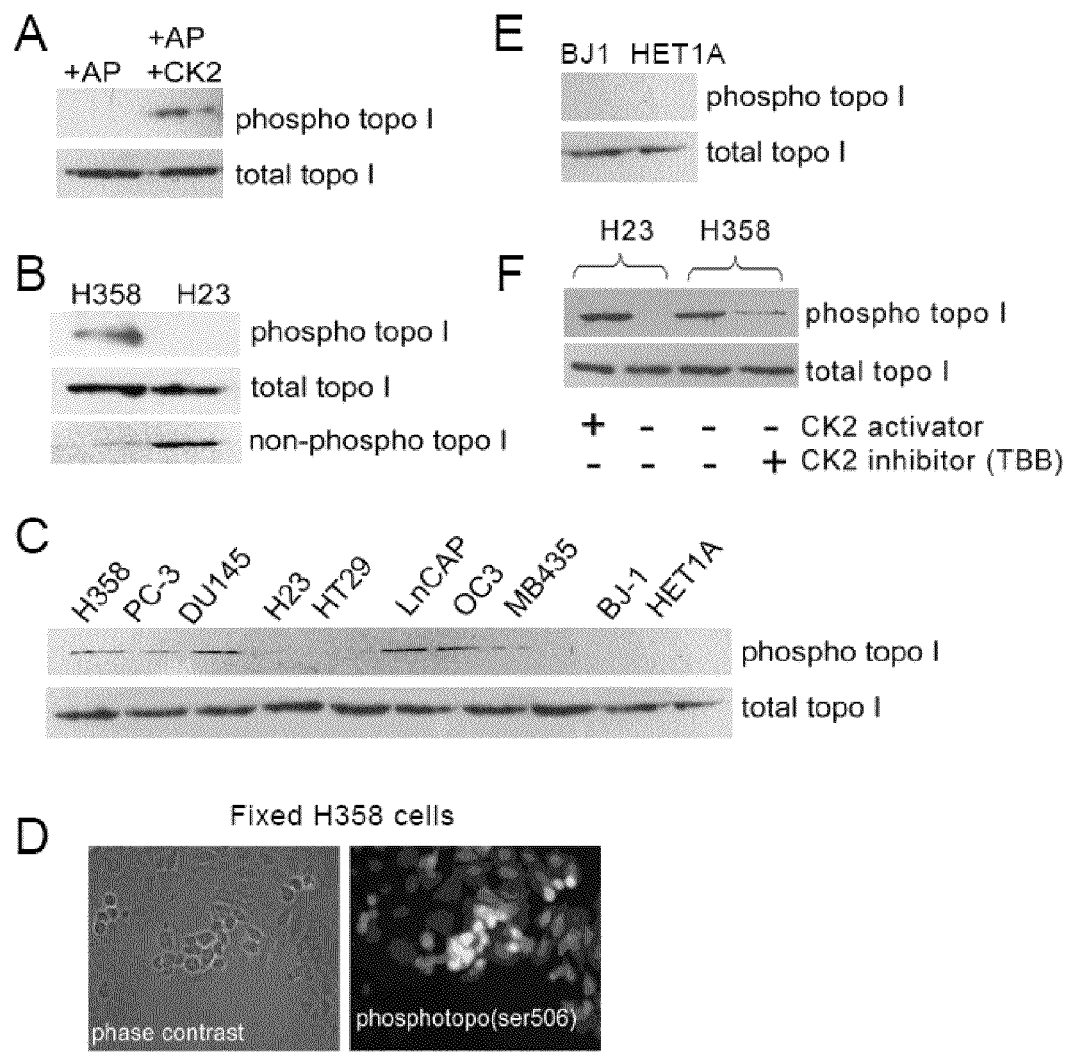
FIG. 14A shows a Western analysis of recombinant, baculovirus-expressed human topo I, dephosphorylated with alkaline phosphatase (+AP) or dephosphorylated with AP followed by rephosphorylation with CK2 (+AP+CK2), using the topo I ser506 phosphospecific antibody (top), and an antibody to total topo I (bottom).
FIG. 14B shows a Western analysis of cellular topo I from H358 and H23 non small cell lung cancer cells using the topo I ser506 phosphospecific antibody (top), an antibody to total topo I (middle), and a control antibody to the non phosphorylated topo I ser 506 site (bottom).
FIG. 14C shows a Western analysis of cellular topo I from a series of human cancer cell lines and normal cells (BJ-1 and HET1A) using the topo I ser506 phosphospecific antibody (top), and an antibody to total topo I (bottom).
FIG. 14D shows immunofluorescence staining of H358 cells with the topo I ser506 phosphospecific antibody (1:100). Cells were fixed and permeabilized as described in Lee, et al., Cancer Research 2005; 65:9834-9842, followed by 2 minute denaturation with 0.5% SDS. Secondary antibody was anti-rabbit IgG Alexafluor 486 (Molecular Probes, Inc.). Cancer cell lines are as follows: H358 non small cell lung cancer, PC-3 prostate cancer, DU145 prostate cancer, H23 non small cell lung cancer, HT29 colon cancer, LnCAP prostate cancer, OC3 esophageal cancer, MB435 breast cancer (abbreviated from MDA MB 435).
FIG. 14E shows a Western analyses of phospho topoisomerase I (using the topo I ser506 phosphospecific antibody, top), and total topoisomerase I (bottom) in lysates of immortalized normal cell lines BJ1 (human fibroblasts) and HET1A (human epithelial cells).
FIG. 14F shows a Western analysis of phospho topoisomerase I (using the topo I ser506 phosphospecific antibody, top) and total topoisomerase I (bottom) in lysates of H23 cells with or without treatment with the CK2 activator as in FIG. 13B, and in lysates of H358 cells with or without treatment with the CK2 inhibitor, TBB, as in FIG. 13A.

As demonstrated herein, the phospho-specific IgG is immunoreactive with cellular topo I from the camptothecin-sensitive H358 cell line, but not with cellular topo I from the camptothecin-resistant H23 cell line, following Western analysis of cell lysates (FIG. 14B), producing, in the case of H358, a single immunoreactive band. In contrast, the control, non-phospho-specific IgG is poorly immunoreactive with H383 topo I, but strongly immunoreactive with H23 topo I, following Western analysis of cell lysates (FIG. 14B). The phospho-specific antibody lacks immunoreactivity with topo I from the immortalized normal cell lines, BJ-1 and HET1A, indicating that the phosphorylated epitope is absent from these normal cells.

A functional relationship between CK2 activation and the expression of the phosphoserine 506 epitope was demonstrated by showing that experimental activation of CK2 in H23 cells treated with the CK2 activator (1-ethyl-4,5-dicarbamoylimidazole) induces cellular levels of the phosphoserine 506 epitope (FIG. 14E), and experimental inhibition of CK2 in H358 cells treated with tetrabromobenzotriazole (TBB) suppresses cellular levels of the phosphoserine 506 epitope (FIG. 14E).

The phosphospecific IgG is immunoreactive with endogenous topo I in fixed, permeabilized H358 cells, as shown by the immunofluorescence image in FIG. 14D, indicating that it can be employed in multiple formats to detect the phosphorylated epitope. Taken together, the results support a model in which abnormal CK2-mediated phosphorylation of topo I on serine 506 in cancer cells expressing elevated CK2 activity leads to elevated topo I activity and increased cellular sensitivity to camptothecin.

The phosphorylated serine 506 site appears to be cancer specific, suggesting additional applications for early diagnosis. An earlier published study identified topo I serine phosphorylation sites at amino acid positions 10, 21, 112, and 394, mediated by either CK2 (ser 10), PKC (ser 21) or cdk1 (ser 112 and 394) (Hackbarth, et al., J Biol Chem 2008; 283: 16711-16722). The present inventors have observed that the A549 and K562 cancer cell lines used to identify these other serine phosphorylation sites, display low levels of topo I phosphorylation and activity similar to levels observed in the poorly phosphorylated H23 cancer cell line, and in the normal cell lines GT41F, BJ-1, and HET1A. Furthermore, the Hackbarth, et al. study found that the phosphorylated protein was some two-fold more active than the dephosphorylated protein, and that the effect was mediated entirely by phosphorylation at position 21, a PKC site. Thus, the CK2-targeted site that the present inventors have identified at position 506 is distinct from the previously identified sites, and is likely to represent an aberrant phosphorylation event characteristic of cancer cells that overexpress CK2.

The topo-I phosphorylation on serine 506 appears to be a common minimal requirement for camptothecin sensitivity, and that cells that lack this phosphorylation site will be resistant to camptothecin. Therefore, a diagnostic assay to detect this phosphoserine epitope can distinguish patients likely to respond to camptothecin-based therapies from patients unlikely to respond, and can guide physicians in the choice of treatment strategies.

The serine 506 epitope of topo I can be exploited for the development of assays, such as immunoassays, to identify patient's tumors that are likely to respond to topo I targeted drugs. The topo I serine 506 assay can be performed on cancer cells or tumor biopsies derived from the patient, or other biological samples from the patient, such as blood, serum, urine, and/or sputum. The clinical application of the assay based on phosphorylation of serine 506 can provide a straightforward and valuable tool for identifying patients most likely to respond to such therapies, and for tailoring improved, individualized treatment regimens. The assay can also be used in the neoadjuvant setting on biopsy material to aid in the choice of therapy prior to surgery.

An antibody-based assay can be utilized in determining the sensitivity of a patient's cancer to a topoisomerase I inhibitor. The antibody-based assay can provide direct identification of the phosphoserine 506 epitope, an unambiguous indicator of a functional state of the topo I that is mechanistically linked to the generation of toxic camptothecin-stablized cleavage complexes.

Alternative or complementary assays to detect CK2 protein, RNA, or activity levels can provide additional indication of camptothecin sensitivity. For example, CK2 RNA expression can be evaluated by semi-quantitative and quantitative PCR across a panel of samples with previously characterized topo I phosphorylation status and camptothecin sensitivity. Protein analysis of CK2 protein may be carried out by Western analysis. RNA can be isolated from formalin-fixed, paraffin-embedded tissues as described in Korbler, et al., Experimental and Molec Pathol 2003; 74:336-340, or from frozen tissue as described in Huang, et al., J Cell Mol Med 2009; 13:398-409. Semi-quantitative or quantitative PCR can be carried out as described in Huang, et al., J Cell Mol Med 209; 13:398-409, using CK2 primers described in Kramerov, et al., Am J Pathol 2006; 168:1722-1736.

In one embodiment of the assay for determination of sensitivity of a cancer cell to a topoisomerase I inhibitor, the status of phosphorylation on serine 506 amino acid residue of topoisomerase I can be visually identified. For example, to prepare an ELISA assay, polystyrene microtiter plates can be coated with 50 μl of varying concentrations (10 μg/ml to 50 μg/ml) of goat anti-topo-1 (in high pH bicarbonate buffer) as the capture antibody, following procedures described in Dudouet, et al., Cancer Res 1990; 50:438-443. Following washing, plates can be incubated with extracts of patient tumor cells (obtained from a biopsy) or patient blood, serum, urine, and/or sputum. This may be followed by treatment with either purified rabbit anti-topo I phosphoser 506 IgG or with anti-topo I nonphosphoser 506 IgG. Alternatively, mouse monoclonal IgGs to these epitopes can be used. The interaction can be detected colorimetrically using a biotinylated anti-rabbit IgG (for example, Rabbit Link, Biogenix, San Ramon, Calif.) and streptavidin-conjugated Horse radish peroxidase (HRP) (for example, from Biogenix, San Ramon, Calif.), which binds to the detection antibody. Finally, a colorimetric HRP substrate, o-phenylenediamine dihydrochloride can be added for 20 minutes, yielding a yellow product detected by absorbance at 492 nm. The reaction may be stopped by the addition sulfuric acid. As alternative approaches, one can employ the ser506 epitope-specific rabbit antibodies as the capture antibodies, followed either by goat or mouse anti-topo I followed by the appropriate biotinylated detection antibody.

An immunofluorescence-based or immunohistochemistry-based assay applicable to frozen or paraffin-embedded tumor biopsies can also be used. This approach requires minimal amounts of material, and allows for the detection of minor subpopulations that could be missed in pooled samples, offering an advantage in certain settings. Frozen sections can be processed using the methods previously detailed (see Lee, C., et al., Cancer Res 2005; 65:9834-9842), involving fixation with formaldehyde, permeabilization with non-ionic detergent, and partial denaturation of proteins with SDS to allow for exposure of internal epitopes (procedures for denaturation have been described in Donaldson, J. R., et al., 1998, Current Protocols in Cell Biology pp. 4.3.1 to 4.3.6, John Wiley and Sons, Inc). Primary antibody treatment can then be Carried out, e.g., with polyclonal rabbit anti topo I phospho ser506), or anti-topo I nonphospho ser 506, or with a general rabbit anti-topo I antibody, followed by secondary antibody staining with goat anti-rabbit IgG Alexa fluor 486 (for example from Molecular Probes, Inc., Eugene, Oreg.). Controls can include secondary antibody only. Slides can be counterstained with the nuclear stain Hoescht 33342, mounted with coverslips and examined by fluorescence microscopy.

For paraffin-imbedded sections, one can use immunohistochemical procedures described in Lebedeva, et al. Human Gene Therapy 2001; 12:762-772. Briefly, slides can be deparafinized at 60° C. for 1 hour, followed by rehydration by sequential passage through xylene, ethanol (100%, 95%, 80%), $H_2O$, and PBS. They can then be treated with 3% $H_2O_2$, blocked with Superblock (Scytec Laboratories, Logan, Utah), and treated with the desired rabbit polycloncal primary IgG, followed by treatment with biotinylated goat anti IgG (for example, Multilink, Biogenix, San Ramon, Calif.) followed by treatment with streptavidin-conjugated horse radish peroxidase (HRP) (for example, from Biogeneix). Slides can then be incubated with the HRP substrate 3-amino-9-ethylcarbazole for colored development. They can then be rinsed and mounted with coverslips with a standard aqueous mounting medium.

One or more samples of cancer cells can be screened for identification of each sample as being sensitive or resistant to a topoisomerase I inhibitor. When phosphorylation of serine 506 amino acid residue of topoisomerase I in one sample is above a predetermined threshold as determined by the assay, that sample can be identified as being sensitive to the topoisomerase I inhibitor. Conversely, when phosphorylation of serine 506 amino acid residue of topoisomerase I in another sample is below the predetermined threshold as determined by the assay, that sample can be identified as being resistant to the topoisomerase I inhibitor. The predetermined threshold may be a ratio of unphosphorylated topoisomerase I to phosphorylated topoisomerase I within the cancer cells of a sample. In this way, a cancer cell sample can be identified as being sensitive to the topoisomerase I inhibitor when the ratio is less than 1, and another cancer cell sample can be identified as being resistant to the topoisomerase inhibitor I when the ratio is greater than 1.

In an antibody based assay, the presence or absence of phosphorylation on serine 506 amino acid residue of topoisomerase I can determined by an antibody that binds phosphorylated serine 506 amino acid residue of topoisomerase I, but does not bind nonphosphorylated serine 506 amino acid residue of topoisomerase I. Alternatively, the presence or absence of phosphorylation on serine 506 amino acid residue of topoisomerase I can determined by an antibody that binds unphosphorylated serine 506 amino acid residue of topoisomerase I, but does not bind phosphorylated serine 506 amino acid residue of topoisomerase I. The antibody based assay may utilize monoclonal or polyclonal antibodies disposed to determine the presence or absence of phosphorylation on serine 506 amino acid residue of topoisomerase I. By way of example, monoclonal antibodies can be produced to phosphorylated serine 506 epitope and also to non-phosphorylated serine 506 epitope, and their abilities can be tested to identify cell lines with high and low topo I activity and/or high and low sensitivity to camptothecin, respectively, using immunoblot (Western), ELISA, and immunofluorescence of fixed cells (Wong and Berkenblit, Oncologist 2004; 9:68-79). Preferably, in order to provide a consistent and stable supply of antibody, a mouse monoclonal to the phosphorylated serine 506 epitope can be generated following standard procedures (Harlow, E., Lane, D. (1999) Using Antibodies: A Laboratory Manual, Cold Spring Harbor Laboratory; Nelson, P. N., Reynolds, G. M., Waldron, E. E., Ward, E., Giannopoulos, K., and Murray, P. G. (2000) Monoclonal antibodies. Mol Pathol 53, 111-117).

Treatment of Cancer Patients

The determination of the status of phosphorylation on serine 506 amino acid residue of topoisomerase I can be utilized in other applications as well, such a treatment of cancer patients. The status of phosphorylation on serine 506 amino acid residue of topoisomerase I can be determined by assaying a biological specimen from the patient, e.g., tumor cells, tumor tissue, blood, serum, urine, and/or sputum. In this way, the patient can be identified as being sensitive to a topoisomerase I inhibitor when phosphorylation of serine 506 amino acid residue of topoisomerase I is above a predetermined threshold as determined by the assay. Patients identified as being sensitive can then be administered with the topoisomerase I inhibitor as part of cancer treatment.

For cancer patients who are less sensitive or resistant to the topoisomerase I inhibitor therapy, increasing their sensitivity to the topoisomerase inhibitor can be included in their treatment. For example, a CK2 activator can be administered to the cancer patient in an amount sufficient to decrease ratio of unphosphorylated topoisomerase I to phosphorylated topoisomerase I, which may make the patient more sensitive to the topoisomerase I inhibitor. An exemplary dose may be in the range of between about 2 mg to about 20 mg per kg of body weight, equivalent to between about 70 mg to about 700 mg per meter squared of body surface area. A preferred amount can be about 100 mg per meter squared of body surface area. For example, 1-ethyl-4,5-dicarbamoylimidazole is one CK2 activator that may be utilized for the treatment of cancer patients that are less sensitive or resistant to the topoisomerase I inhibitor therapy.

EXAMPLES

Example 1

Defective ARF/Topoisomerase I Complex Formation in H23 Cells

FIG. 1A shows a silver stained gel following a pull-down assay in which immobilized human ARF-thioredoxin fusion protein (or the N-terminal domain (1-64) of ARF) was used to compare ARF-binding proteins from DU145 (prostate cancer), H358, and H23 (non-small cell lung carcinoma) cell RIPA lysates.

Topoisomerase I bound to full-length ARF (ARF, FIG. 1A) but not the ARF N-terminal domain (ARF-N-term, amino acid residues 1-64, FIG. 1A) encoded by ARF's first exon (exon 1β). This is consistent with previous reports that topoisomerase I binds to ARF through the ARF C-terminal, exon 2-encoded domain (Ayrault, et al., Oncogene 2006; 25(19): 2827 (correction); Olivier, et al., Oncogene 2003; 22(13): 1945-54). H23 cells appeared to have significantly less topoisomerase I activity compared to that measured in H358 cells (FIG. 1A, far right lane).

Western blot analysis confirmed that the level of topoisomerase I was reduced in the fraction pulled down by immobilized ARF from H23 cells compared to H358 cells (FIG. 1B, left panel). However, total endogenous topoisomerase protein levels in H23 and H358 cells RIPA lysates were similar (FIG. 1B, right panel). Furthermore, a complete sequence analysis of the 2,295 base pair coding sequence of topoisomerase I in H23 cells showed that the sequence corresponded to the wild-type topoisomerase I sequence (EC.5.99.1.2, Accession # NM_003286). Thus, reduced binding of topoisomerase I from H23 cells to immobilized ARF is not the result of reduced cellular levels of topoisomerase I nor is it the result of a mutation in topoisomerase I that could alter its binding properties.

FIG. 1C shows the results of a co-immunoprecipitation experiment using DNAse I solubilized nuclear extracts. This cellular fraction contains more than 95% of topoisomerase I and ARF (Ayrault, et al., Oncogene 2004; 23(49):8097-104). ARF-topoisomerase I complexes were readily detectable in H358 nuclear extracts, but were undetectable in H23 nuclear extracts (left panel, FIG. 1C). Thus, the failure of topoisomerase I from H23 cell lysates to bind immobilized ARF is reflected in the lack of endogenous ARF/topoisomerase I complexes.

To determine whether overexpressed ectopic ARF could drive topoisomerase I into complexes with ARF in H23 and H358 cells, cells were treated with an Adp14 adenoviral vector (moi, 20 pfu/cell) for 4 hours and prepared nuclear extracts 48 hours later. Co-immunoprecipitation analysis followed by Western analysis showed that ARF-topoisomerase I complexes increase about 3 fold in H358 cells following treatment with Adp14; indicating that not all cellular topoisomerase I had been bound by ARF in untreated cells (FIG. 1C middle panel). ARF-topoisomersase I complexes remained undetectable in H23 cells (FIG. 1C middle panel).

The material that remained unbound following two successive immunoprecipitations with anti-topoisomerase I was also analyzed (FIG. 1C, right-hand panel (unbound)). Undetectable amounts of ARF protein in H358 cells were found in the unbound material, indicating that virtually all cellular ARF was complexed with topoisomerase I. In contrast, in H23 cells, virtually all the cellular ARF was found in the unbound material. Taken together, these result demonstrate that the failure of H23 cells to form ARF-topoisomerase I complexes, which are required for topoisomerase I activity, are not a result of reduced ARF or topoisomerase levels, nor are they a result of inactivating mutations in either protein.

Vectors: The Adp14 vector encoding full-length ARF, the Ad1β vector encoding the 64-amino acid residue N-terminal domain of ARF (ARF N-term), and vector treatment conditions have been described (Saadatmandi, et al., Cancer Gene Ther 2002; 9(10):830-9; Huang, et al., Cancer Research 2003; 63:3646-3653). Equal titers of Adp14 and Ad1β were confirmed by RT-PCR to produce equivalent levels of ARF and ARF N-term message. An siRNA expression plasmid specific for the exon 2-encoded region of ARF (pKD-Ink4a-v2), as well as a negative control siRNA expression plasmid (pKD-NegCon-yl) were purchased from Upstate, Temecula, Calif., and transfected into cells using Lipofectamine™ (Invitrogen, Carlsbad, Calif.) according to the manufacturer's instructions. An siRNA to the exon 1βregion of ARF (sense sequence: 5'-GGGUUUUCGUGGUUCACAUtt-3' (SEQ ID NO: 4); antisense sequence: 5'-AUGUGAACCAC-GAAAACCCtc-3' (SEQ ID NO: 5)) was purchased from Ambion, Inc., Austin Tex.

Co-Immunoprecipitation/Western: DNAse I-solubilized nuclear extracts were prepared according to reference (Ayrault, et al., Oncogene 2004; 23(49):8097-104). Briefly, cells ($10^6$) were harvested and lysed in DNAse I solubilization buffer (10 mM Hepes pH 7.5, 100 mM NaCl, 300 mM sucrose, 3 mM $MgCl_2$, 1 mM EDTA, 1 mM DTT, 0.5% Triton X-100, 1 mM phenylmethylsulfonyl fluoride (PMSF), complete protease inhibitors (Roche, Nutley, N.J.), followed by centrifugation to pellet nuclei. Nuclei were resuspended in 300 µl. of the same buffer, treated with 1 mg/mL DNAse I (Sigma, St. Louis, Mo.) for 15 minutes at 37° C., and centrifuged. The DNAse I-solubilized material, which contained the bulk of cellular topoisomerase I and ARF protein (Ayrault, et al., Oncogene, 2004; 23(49):8097-104), was used for immunoprecipitation. (We found that high salt-extracted nuclei (see subnuclear fractionation and topoisomerase I assays, below) and DNAse I-solubilized nuclei were similar with respect to topoisomerase I and ARF recovery; however, DNAse I solubilization avoided the use of high salt concentrations that would disrupt complexes). Co-immunoprecipitation was carried out in 1 mL of the same buffer, overnight at 4° C. with rocking, containing 175 μg protein and 20 μL of antibody following our previously described procedure (Lee, et al., Cancer Res 2005; 65(21):9834-42). Where bound and unbound fractions were to be compared, the extracts were subjected to 2 successive treatments with antibody (anti-topoisomerase I or anti-NPM), were found to be sufficient to deplete extracts of immunoreactive material. The immunoprecipitated material from the $1^{st}$ and $2^{nd}$ treatments was pooled and designated "bound". Immunoprecipitates were incubated an additional hour in the presence of 80 μL protein G agarose (Santa Cruz Biotechnology), centrifuged and washed with PBS, resuspended in SDS-PAGE sample buffer, boiled, electrophoresed on a 12.5% SDS-PAGE gel, and subjected to Western analysis as described previously (Saadatmandi, et al., Cancer Gene Ther 2002; 9(10):830-9). The material that did not immunoprecipitate was designated "unbound" and was concentrated by precipitation with 5 volumes of acetone, prior to resuspension in sample buffer. Antibodies were: Goat polyclonal anti-topoisomerase I (Santa Cruz Biotechnology, Santa Cruz, Calif.), mouse monoclonal anti-nucleophosmin (NPM, B23) (Sigma, St. Louis, Mo.), rabbit polyclonal anti-full length ARF (Zymed Laboratories, Inc, South San Francisco, Calif.), mouse monoclonal anti-phosphoserine (Sigma, St. Louis, Mo.). All primary antibodies were used at 1:100 for Westerns. Secondary antibodies for Westerns were goat anti-rabbit, goat anti-mouse, and donkey anti-goat (all purchased from Santa Cruz Biotechnology, Santa Cruz, Calif.) and were used at 1:1000.

Subnuclear fractionation: Isolation of nuclei and preparation of nuclear extracts were carried out as described in reference (Olnes, et al., Biotechniques 1994; 17(5):828-9), by swelling cells in hypotonic buffer (10 mM Hepes pH 7.9, 10 mM KCl, 0.1 mM EDTA, 0.1 mM EGTA, 1 mM DTT, 0.5 mM Phenylmethylsulfonyl fluoride (PMSF), complete protease inhibitors (Roche, Nutley, N.J.)), and lysing cells by adding 0.6% NP40 to the hypotonic buffer, followed by centrifugation to recover nuclei. For the topoisomerase I assays, nuclei were then extracted for 1 hour on ice in high salt buffer (20 mM Hepes pH 7.9, 0.4 M NaCl, 1 mM EDTA, 1 mM EGTA, 1 mM DTT, 1 mM PMSF, 10% glycerol, and complete protease inhibitors). For storage, nuclear extracts were adjusted to 50% glycerol and placed at −80° C. until used. For preparation of nucleolar and nucleoplasmic fractions, the NP40-prepared nuclei were centrifuged through sucrose, sonicated, and fractionated by centrifugation again through sucrose as described in reference (Andersen, et al., Curr Biol 2002; 12(1):1-11). Nucleoli were recovered in the pellet, and the unpelleted material (nucleoplasm) was concentrated by precipitation with 5 volumes of acetone.

Example 2

H23 Nuclear Extracts have Reduced Topoisomerase I Activity which Cannot be Stimulated by ARF H23 and H358 nuclear extracts were compared for topoisomerase I activity in vitro, and investigated whether the activities could be stimulated by the addition of recombinant thioredoxin-ARF. As shown in FIG. 2A, H358 topoisomerase I was found to be more effective at relaxing supercoiled plasmid DNA than was H23 topoisomerase, achieving 50% relaxation at about 0.06 μg nuclear extract per reaction, some 10-fold lower than the amount of H23 extract needed to achieve the same level of relaxation (0.6 μg extract per reaction). A typical electrophoretic profile of the reaction products with increasing amounts of nuclear extract is shown in FIG. 2B in which 0.32, 0.65, or 1.3 μg of H358 cell extract (lanes 1-3) or H23 (lanes 4-6) were added in each reaction. "r" is the relaxed (non-supercoiled) plasmid and "s" is the supercoiled form.

Similar assays were carried out using the amount of each respective nuclear extract that produced a 50% conversion of supercoiled to relaxed form (0.06 and 0.6 μg extract protein per reaction for H358 and H23, respectively), and added increasing amounts of purified thioredoxin-ARF (3, 9, 27 ng). As a control, in separate assays, increasing amounts of thioredoxin-ARF-N-terminus, which does not bind to topoisomerase I, was added. Thioredoxin-ARF enhanced the activity of H358 topoisomerase in a dose-dependent manner (FIG. 2C, lanes 1-3), but had no effect on H23 topoisomerase (FIG. 2C, lanes 4-6), as expected based on the inability of ARF to bind to H23 topoisomerase. Neither H358 not H23 topoisomerase activities responded to the addition of thioredoxin ARF-N-terminus at similar doses (FIG. 2C lanes 7-12).

Topoisomerase I assays: Assays were carried out using the Topoisomerase I Assay Kit (Topogen, Fla.), according to the instructions provided with the kit and using the high salt nuclear extracts prepared as described above. Briefly, 0.125 μg supercoiled plasmid DNA was incubated with 0-1.3 μg of nuclear extract for 30 minutes at 37° C. The reaction was stopped by adding stop loading dye supplied in the kit and electrophoresed on a 1% agarose/TAE (10 mM TRIS-acetate/1 mM EDTA) gel until the dye front had reached the bottom of the gel. The gel was then stained for 20 minutes in 0.5 μg/mL ethidium bromide, destained in deionized water for 30 minutes, and electrophoresed for an additional hour to enhance band visibility. The gel was photographed and band intensities were analyzed digitally using a Kodak digital camera and analysis software. Some assays were carried out with alkaline phosphatase-treated extracts, prepared as described below, or in the presence of ARF or ARF1β thioredoxin fusion proteins (3, 9, 27 ng), prepared as described above (see pull-down assays).

Example 3

Topoisomerase I is Activated by Both Phosphorylation and ARF Binding

A topoisomerase I immunoprecipitation analysis followed by Western detection of phosphoserine revealed that H358 cells expressed a serine-phosphorylated topoisomerase I (FIG. 3A, lane 1, top row). A similar analysis of phosphotyrosine revealed no evidence for tyrosine phosphorylation (data not shown). Similar results were found in PC-3 cells (data not shown). In contrast, serine-phosphorylated topoisomerase I was only weakly detectable in H23 cells (FIG. 3A, lane 2, top row).

Treatment of both H358 and H23 nuclear extracts with alkaline phosphatase (AP) eliminated serine phosphorylation (FIG. 3A, lanes 3, 4, top row) and abolished their topoisomerase I activity in vitro (FIG. 3B, lanes 4-6 and lanes 13-15). The dephosphorylated topoisomerase I from H358 cells could no longer be activated by addition of increasing amounts of ARF fusion protein (FIG. 3B, lanes 7-9). Furthermore, while topoisomerase I co-immunoprecipitated with ARF from untreated H358 nuclear extracts (FIG. 3A, lane 1, middle row), it failed to co-immunoprecipitate with ARF from H358 nuclear extracts treated with alkaline phosphatase (FIG. 3A, lane 3, middle row). Topoisomerase I failed to co-immunoprecipitate with ARF from either untreated or alkaline phosphatase-treated H23 cell nuclear extracts (FIG. 3A, lanes 2,4, middle row).

When alkaline phosphatase-treated extracts from either H358 or H23 cells were treated with casein kinase II (CKII), a serine kinase, we observed restoration of serine phosphorylation (FIG. 3A, lanes 5,6, top row) and restoration of ARF/topoisomerase I complex formation (FIG. 3A, lanes 5,6, middle row). Recovery of topoisomerase I following immunoprecipitation was the same in all cases (FIG. 3A, lanes 1-6, bottom row).

Alkaline phosphatase treatment of purified recombinant human topoisomerase I, abolished serine phosphorylation (FIG. 3C, lane 1, top row), and abolished its ability to bind recombinant ARF fusion protein (FIG. 3C, lane 1, middle row). But, serine phosphorylation and ARF binding could be restored by treatment with casein kinase II (FIG. 3C, lane 2, top and middle rows, respectively). Recovery of topoisomerase I following immunoprecipitation was the same in all cases (FIG. 3C, lanes 1, 2 bottom row). Finally, a topoisomerase I IP/Western analysis was carried out on lysates of an additional cell line, HT29, of colon adenocarcinoma origin. The results revealed a reduced level of serine phosphorylated topoisomerase I that correlated with failure to bind ARF, a result similar to what was seen with H23 cells. Taken together, the results establish that differences in topoisomerase I serine phosphorylation account for the differences in ARF/topoisomerase I complex formation in observed in the cell lines examined.

Casein kinase II assays: $10^6$ cells were harvested, resuspended in 400 µl 10 mM Tris pH 7.4, and subjected to 3 cycles of freeze/thaw. 50 µg of cell extract was assayed for casein kinase II (CKII) activity using the CKII Assay kit from Upstate (Temecula, Calif.), following procedures supplied with the kit.

Example 4

Variable CKII Levels Account for the Differences in Topoisomerase Activity Among Cell Lines Additional assays were performed to determine whether the reduced levels of topoisomerase I serine phosphorylation in H23 and HT29 cells could be due to a reduced cellular levels of casein kinase II (CKII). As shown in FIG. 3D, H23 cell lysates display some 7% of the CKII activity of H358, and HT29 cells display some 41% of the activity of H358. The results indicate that low levels of CKII activity are likely to be responsible for the reduced levels of topoisomerase I serine phosphorylation and reduced ARF/topoisomerase I complex formation in H23 and HT 29 cells.

Example 5

Phosphorylated Topoisomerase I Retains ARF in the Nucleolus

Western analyses of ARF in subnuclear fractions, as well as immunofluorescence staining of ARF in fixed H358 and H23 cells was performed to assess whether the interaction between ARF and topoisomerase I affects subnuclear distribution. For Western analyses, nuclei were prepared as for the topoisomerase I assay, followed either by salt extraction to obtain total nuclear proteins, or by further subfractionation into nucleoplasmic and nucleolar fractions.

FIG. 4A shows the results of Western analyses carried out on total nuclear and subnuclear fractions. Topoisomerase I and ARF levels were comparable in H358 and 1-123 cells (FIG. 4A, left lanes). Cytoplasmic levels of ARF and topoisomerase I were low to undetectable (not shown). Topoisomerase I was concentrated in the nucleolar fraction in both H358 and H23 cells (FIG. 4A, top row). While ARF was also concentrated in the nucleolar fraction in H358 cells, it appeared to be evenly distributed between nucleolar and nucleoplasmic fractions in H23 cells (FIG. 4A, bottom row). This result was confirmed by immunofluorescence microscopy of fixed cells (FIG. 4B).

Nuclei were stained with the DNA stain, Hoechst 33342, which is excluded from nucleolar regions (top panels). Using an anti-ARF antibody, ARF was detected in a predominantly nucleolar staining pattern in H358 cells (FIG. 4B, bottom left). By contrast, in H23 cells, anti-ARF staining was found across the entire nuclear and perinuclear region (FIG. 4B, bottom right). Thus, failure of ARF to bind topoisomerase I correlates with delocalization of ARF throughout the nucleus, suggesting that topoisomerase contributes to the tethering of ARF in the nucleolus.

The interaction between ARF and nucleophosmin (NPM, B23), an abundant nucleolar protein, was examined in H358 and H23 cells. Nuclear extracts of H358 and H23 cells were immunoprecipitated with two successive treatments with anti-NPM antibody, followed by Western detection of NPM and ARF in the pooled immunoprecipitated material (bnd) or in the material that remained unbound following two successive immunoprecipitations (un).

In H358 cells, virtually all of the cellular ARF was recovered in the material that co-immunoprecipitated with NPM, with undetectable levels recovered in the unbound material (FIG. 4C). This result is consistent with a previous report in murine fibroblasts that the majority of cellular ARF is bound to NPM (Bertwistle, et al., Mol Cell Biol 2004; 24(3):985-96). In H23 cells, however, ARF was detected in approximately equivalent levels in the NPM-bound and unbound fractions (FIG. 4C), consistent with its decreased nucleolar localization. Because the majority of cellular ARF in H358 cells could also be recovered in complexes with topoisomerase I (FIG. 1C, compare left and right panels), it is possible that topoisomerase I, ARF, and NPM are present together in a larger complex in H358 cells, and that defective binding of ARF to topoisomerase I in H23 cells destabilizes other interactions of ARF within the complex, including the interaction with NPM. Taken together, the results indicate that binding of ARF to topoisomerase I is required to maintain ARF's full nucleolar localization and its interaction with NPM.

Example 6

ARF Mediates Sensitivity to Topoisomerase I Inhibitors

Adenoviral vectors were used to achieve ectopic overexpression of full-length ARF (Adp14) or ARF-N-terminal domain (Ad1β), and RNA interference to down-regulate endogenous expression of ARF. As shown by the Western analysis of H358 cells in FIG. 5A, ARF levels increased by some 3-fold, as determined by digital analysis of band intensities, by 48 hours post-treatment with Adp14 (moi, 20 pfu/cell, FIG. 5A, lane 1), relative to Ad1β-treated cells (FIG. 5A, lane 2) or untreated cells (FIG. 5A, lane 4). By 72 hours post-transfection of an siRNA expression plasmid to ARF exon 2 (FIG. 5A, lane 5), endogenous ARF levels fell to 0.27 that found in untreated cells (FIG. 5A, lane 4) or control siRNA-treated cells (FIG. 5A, lane 3).

Viability assays were performed 24 hours post-vector treatment by exposing cells for 24 hours to increasing doses of camptothecin (a topoisomerase I inhibitor) in triplicate in a 96-well viability assay, and assaying them for viability 5 days post-start of vector treatment (FIG. 5B). For each growth curve, cell viabilities were normalized to the viability of cells treated with vector only (no camptothecin), to enable a direct visualization of the sensitization effect. As shown for H358 cells in FIG. 5B (left assay), treatment of cells with Adp14 resulted in a greater decrease in cell viability with increasing camptothecin concentrations than did camptothecin alone, while treatment of cells with siRNA to reduce ARF expression resulted in a smaller decrease in cell viability with increasing camptothecin concentrations. Ad1β-treated cells overexpressing the ARF-N-terminal domain that does not interact with topoisomerase I, and control siRNA-treated cells in which levels of endogenous ARF remained unaltered, displayed camptothecin responses similar to cells receiving no vector treatment (FIG. 5B, left).

To verify the generality of these observations, the same series of assays were carried out with the PC-3 prostate cancer cell line (FIG. 5B, right), with similar results. PC-3 cells express active, serine phosphorylated topoisomerase I (data not shown). The siRNA used to down-regulate endogenous ARF, targets the exon 2-encoded region of ARF that is shared by the p16INK4A tumor suppressor. While H358 cells express endogenous p16INK4A, PC-3 cells do not (Chi, et al., Clin Cancer Res 1997; 3(10):1889-97), and they therefore provide a control showing that the observed effect on camptothecin sensitivity can be attributed to ARF, and is not cell specific. As a further siRNA control, we reduced endogenous ARF expression in H358 cells by treating them with an siRNA to exon 1β, which is not shared with p16INK4A, and then restored ARF expression by treatment with Adp14 one day later. As shown in the Western analysis in FIG. 5C, siRNA treatment (lane 3, ARF) reduced ARF protein levels to about 0.25 that of untreated cells (lane 1, ARF) by 72 hours post-siRNA treatment. Digital analyses of ARF band intensities are shown below the ARF lanes. Treatment with Adp14 (moi, 100 pfu/cell) 24 hours after siRNA treatment, restored ARF expression, measured 72 hours post-siRNA treatment, to 1.3-fold that found in untreated cells (lane 2, ARF). Actin levels remained unchanged by these treatments (FIG. 5C, actin).

To assay how these treatments affected camptothecin responses, non-vector-treated cells, siRNA-treated cells, and siRNA+Adp14-treated cells, were exposed to increasing doses of camptothecin as in FIG. 5B and assayed for viability 5 days post-start of vector treatment. As shown by the viability assay in FIG. 5C, reduction in ARF expression in H358 cells following exon 1β siRNA treatment, resulted in decreased sensitivity to camptothecin, while restoration and moderate overexpression of ectopic ARF slightly enhanced sensitivity, supporting the results in FIG. 5B.

Increased camptothecin sensitivity of Adp14-treated H358 cells correlated with about a 3-fold increase in ARF/topoisomerase I complex formation relative to Ad1β-treated, control siRNA treated, or non-vector treated cells, as shown by the IP/Western analysis in FIG. 5D (upper panel, lane 1 versus lanes 2-4), and with an increase in topoisomerase I activity (FIG. 5D, lower panel lane 1 versus lanes 2-4, bars 2-4). The decreased camptothecin sensitivity of siRNA-treated H358 cells correlated with about a 3-fold decrease in ARF/topoisomerase I complex formation (FIG. 5D, upper panel lane 5), and with a decrease in topoisomerase I activity (FIG. 5D, lower panel lane 5, bar 5).

The H23 cell line, with low to undetectable levels of endogenous ARF/topoisomerase I complexes, respectively (see FIG. 1B) displayed a greatly reduced response to camptothecin (FIG. 5E), consistent with studies showing that loss of topoisomerase I phosphorylation reduces activity (Pommier, et al., J Biol Chem 1990; 265(16):9418-22). The fact that H23 cells cannot be sensitized to camptothecin by ectopic overexpression of ARF indicates that ARF-mediated sensitization requires its interaction with active, serine phosphorylated topoisomerase I.

Example 7

ARF Promotes Topoisomerase I DNA Binding

Figure 6:
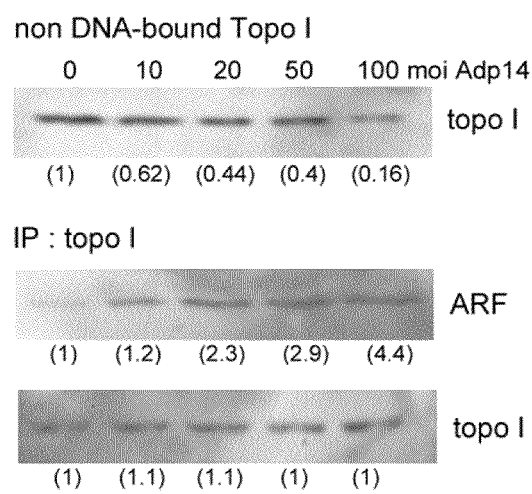
FIG. 6 is a series of electrophoretic gels showing that ARF binding promotes topoisomerase I complex formation with DNA. The top panel shows the results of an immunodepletion assay carried out on nuclei prepared from cells treated with increasing doses of Adp14, followed by camptothecin treatment to crosslink topoisomerase I onto DNA. The gel shows that increasing levels of ARF lead to a reduction in the band intensity of topoisomerase I, indicating that more topoisomerase I has become covalently bound to DNA by camptothecin and therefore cannot enter the gel. The middle and bottom panels show topoisomerase I immunoprecipitation followed by an ARF and a topoisomerase I Western analysis, respectively, in cells treated with increasing doses of Adp14. Digital analyses of topoisomerase I and ARF levels are shown below lanes. The results show that increasing doses of Adp14 promote increasing levels of ARF-topoisomerase I complex formation, and that this promotes increased topoisomerase I binding to DNA following camptothecin treatment.

Topoisomerase I/DNA binding assay were performed to address the mechanism by which ARF activates topoisomerase I. In FIG. 6 shows the results from an immunodepletion assay in which topoisomerase I was trapped in a complex with DNA by treatment of cells with camptothecin, followed by Western analysis of nuclei prepared with NP40. Because topoisomerase I/DNA complexes are too large to enter the gel, an increase in topoisomerase I/DNA complex formation leads to a decrease in the intensity of the topoisomerase I immunoreactive band representing non-DNA-bound topoisomerase I. Treatment of H358 cells with increasing doses of Adp14 resulted in a progressive decrease in non DNA-bound topoisomerase I (FIG. 6 top panel), under conditions where co-immunoprecipitated ARF/topoisomerase I complexes, released from NP40 nuclei by DNase I treatment, increased (FIG. 4A, middle panel), and total topoisomerase I, released from NP40 nuclei by DNase I treatment, remained constant (FIG. 6, bottom panel). Thus increased ARF/topoisomerase I complex formation is accompanied by an increase in DNA bound topoisomerase I. The numbers below the lanes indicate digital analyses of band intensities, relative to the control lane (far left, 0 moi Adp14).

Example 8

Figure 3:
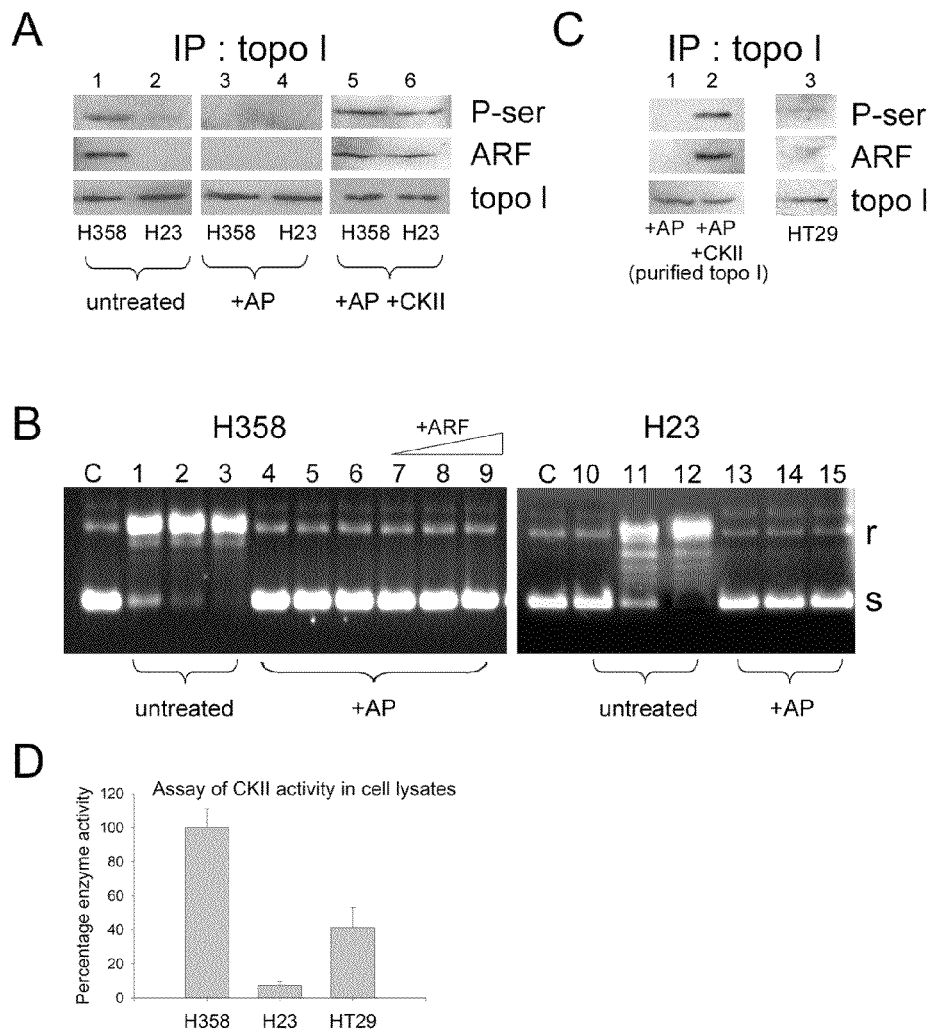
FIG. 3A is an electrophoretic gel showing that ARF binds to topoisomerase I in H358 nuclear extracts, but not in H23 nuclear extracts. The ARF-topoisomerase I complexes are destroyed by alkaline phosphatase (+AP) treatment and restored in both cell types following CKII treatment.
FIG. 3C shows that this effect is also achieved using purified topoisomerase I.
FIG. 3B is an electrophoretic gel showing that the catalytic activity of topoisomerase I in H358 cells is abolished by alkaline phosphatase treatment and the activity cannot be enhanced by overexpression of ARF.
FIG. 3D is a bar graph showing the CKII activity in lysates of H358, H23, and HT29 cells.
Figure 7:
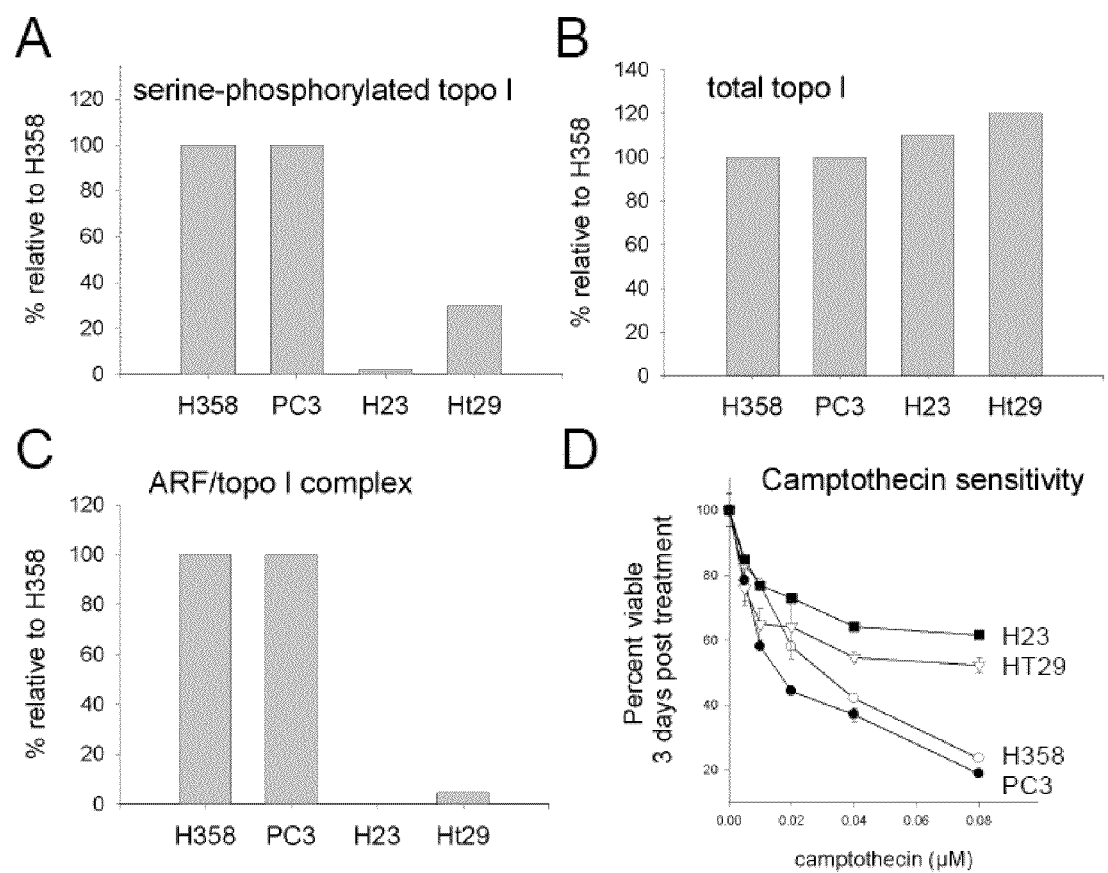
FIG. 7 is a series of graphs showing the correlation of serine phosphorylation, ARF/topoisomerase I complex formation and camptothecin sensitivity.

Camptothecin Sensitivity Correlates with Topoisomerase I Phosphorylation and with ARF Binding FIG. 7 shows the results of an additional topoisomerase I immunoprecipitation (IP)/Western analyses as in FIG. 3, and cell viability assays in the presence of camptothecin. This experiment was performed to confirm the relationship between topoisomerase I serine phosphorylation, ARF/topoisomerase I complex formation, and cellular camptothecin sensitivity. The Western blots were analyzed digitally and the band intensities relative to H358 are plotted as bar graphs in FIG. 7A-7C).

The PC-3 cell line displays a level of topoisomerase I serine phosphorylation similar to H358 (FIG. 7A), a similar level of total cellular topoisomerase I (FIG. 7B), a similar level of cellular ARF/top I complex formation (FIG. 7C), and a similar degree of sensitivity to camptothecin (FIG. 7D). In contrast, both H23 and HT29 cells display a reduced level of topoisomerase I serine phosphorylation compared to H358 (FIG. 7A), although total cellular topoisomerase I is similar to that of H358 and PC-3 (FIG. 7B). H23 and HT 29 cells display reduced levels of cellular ARF/topoisomerase I complex formation (FIG. 7C), and are more resistant to camptothecin that are H358 and PC-3 cells (FIG. 7D).

Example 9

Figure 8:
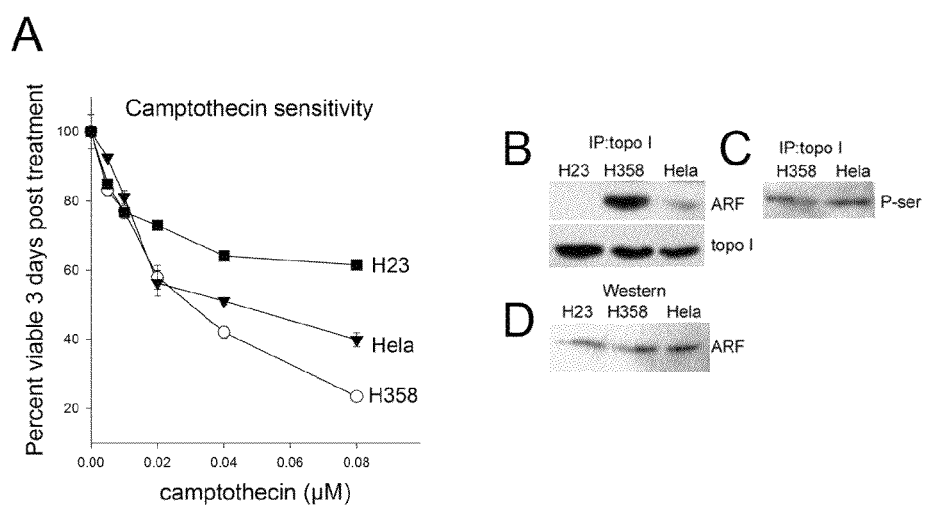
FIG. 8A is a graph showing the viability of the indicated cell types 3 days after treatment with camptothecin.
FIG. 8B is an electrophoretic gel of a topoisomerase I immunoprecipitation followed by an ARF and topoisomerase I Western analysis.
FIG. 8C is an electrophoretic gel of a topoisomerase I immunoprecipiation and a phosphoserine Western analysis.
FIG. 8D is an ARF Western analysis. Together, these data demonstrate that the level of ARF-topoisomerase I complex formation in Hela cells is intermediate to that of H538 and H23 cells. The sensitivity of Hela cells to topoisomerase I inhibitors is also intermediate to that of H538 and H23 cells. The fact that Hela cell topoisomerase I is serine phosphorylated indicates that abnormalities other than serine phosphorylation can disrupt the ARF/topoisomerase I complex and promote resistance to camptothecin.

Hela Cells have Partially Defective ARF-Topoisomerase I Complex Formation and Show Intermediate Sensitivity to Camptothecin Hela cells display a sensitivity to camptothecin intermediate to that of H23 and H358 (FIG. 8A). The assay in FIG. 8A was carried out as in FIG. 7D. ARF/topoisomerase I complex formation was examined using the co-immunoprecipitation assay described for FIGS. 3A and 3C. A reduced but detectable level of ARF/topoisomerase I complex formation in Hela cells was observed, compared to H358 cells (FIG. 8B). ARF/topoisomerase I complex formation in H23 cells was undetectable (FIG. 8B), confirming previous experiments (FIG. 1C). However, topoisomerase I was serine phosphorylated in Hela cells (FIG. 8C), indicating that other factors are likely to be responsible for the failure to form ARF/topoisomerase I complexes. Total ARF levels in H23, H358, and Hela cells were found to be similar (FIG. 8D). The results indicate that defective ARF/topoisomerase I complex formation can result from cellular changes other than defective phosphorylation of topoisomerase I, and correlates with increased resistance to camptothecin.

Example 10

Treatment of Cancer in a Human

A human patient diagnosed with cancer may be treated according to the methods and principles of this disclosure. For example, a patient diagnosed with prostate cancer, lung cancer, colon cancer, or ovarian is administered once each day for five days, by intratumoral injection, $10^5$ to $10^{10}$ viral particles of an adenoviral vector containing nucleic acid encoding functional CMI, operably linked to a promoter. Subsequently, the patient is administered Irinotecan at 100 mg/meter$^2$ weekly for 4 weeks. This treatment regimen results in a reduction in the size of the prostate, lung, colon, or ovarian tumor, or the level of prostate-specific antigen in the blood, or both.

During the course of this treatment regimen, the prostate, lung, colon, or ovarian cancer cells contain both an elevated serine kinase biological activity (caused by treatment with the CKII-containing adenoviral vector) and a topoisomerase inhibitor (i.e., a camptothecin-derived drug such as irinotecan or Topotecan).

Example 11

Camptothecin Sensitivity of Normal and Cancer-Derived Cell Lines and Correlation with Topo I Phosphorylation and CK2 but not PKC or cdk1 Activity and Protein Levels Studies of a large panel of cell lines have shown that cell lines with overexpressed CK2 (FIG. 11B1-B3 and 11C1-C3) display hyper serine phosphorylation of topo I (FIG. 11D) that correlates with sensitivity to camptothecin (FIG. 11A). The cellular levels of two other serine kinases, PKC and cdk1, both of which have been implicated in topo I serine phosphorylation, do not correlate with sensitivity to camptothecin (FIG. 11A-C). Referring to FIG. 11A, 3-day viability assays carried out in 96 well plates as described in Saadatmandi et al (2002) Cancer Gene Therapy 9:830-839. Cells were plated at 2000 cells per well and allowed to attach. Triplicate wells were then treated with the indicated doses of camptothecin for 18 hours, and monitored for viability 3 days post-start of treatment. Viability is represented as a % of control, untreated, cell viability. Referring to FIGS. 11B1-B3, PKC (B1), cdk1 (B2), and CK2 (B3) levels in cancer cell lines: Cell lysates were prepared from the indicated cancer cell lines and assayed for enzymatic activities, or evaluated by Western analysis for total PKC, cdk1, or CK2 protein levels. Actin levels served as a control (same control for PKC, cdk1, and CK2). Referring to FIGS. 11C1-C3 PKC (C1), cdk1 (C2), and CK2 (C3) levels in normal cell lines, compared to H358 and H23: Cell lysates were prepared from the indicated cell lines and evaluated as before. Numbers below Western blots indicate digital reading of band intensities of PCK, cdk1, or CK2 Western blots, relative to H358. Referring to FIG. 11D, topo-I immunoprecipitation followed by topo-I Western (top row) or phosphoserine Western (bottom row). Numbers below Western blot are digital readings of ser-P band intensities relative to H358.

Example 12

CK2 is Necessary and Sufficient to Maintain Topo I Phosphorylation, Enzymatic Activity, and Phosphorylation-Dependent Topo 1 Molecular Interactions In Vivo To determine whether cellular levels of CK2 have functional significance with regard to topo I properties, we examined how experimental modulation of CK2 activity in two representative cell lines, namely camptothecin sensitive H358 cells and camptothecin resistant H23 cells, affects topo I phosphorylation, topo I complex formation with p14ARF, topo I activity, and camptothecin-induced DNA damage.

Figure 15:
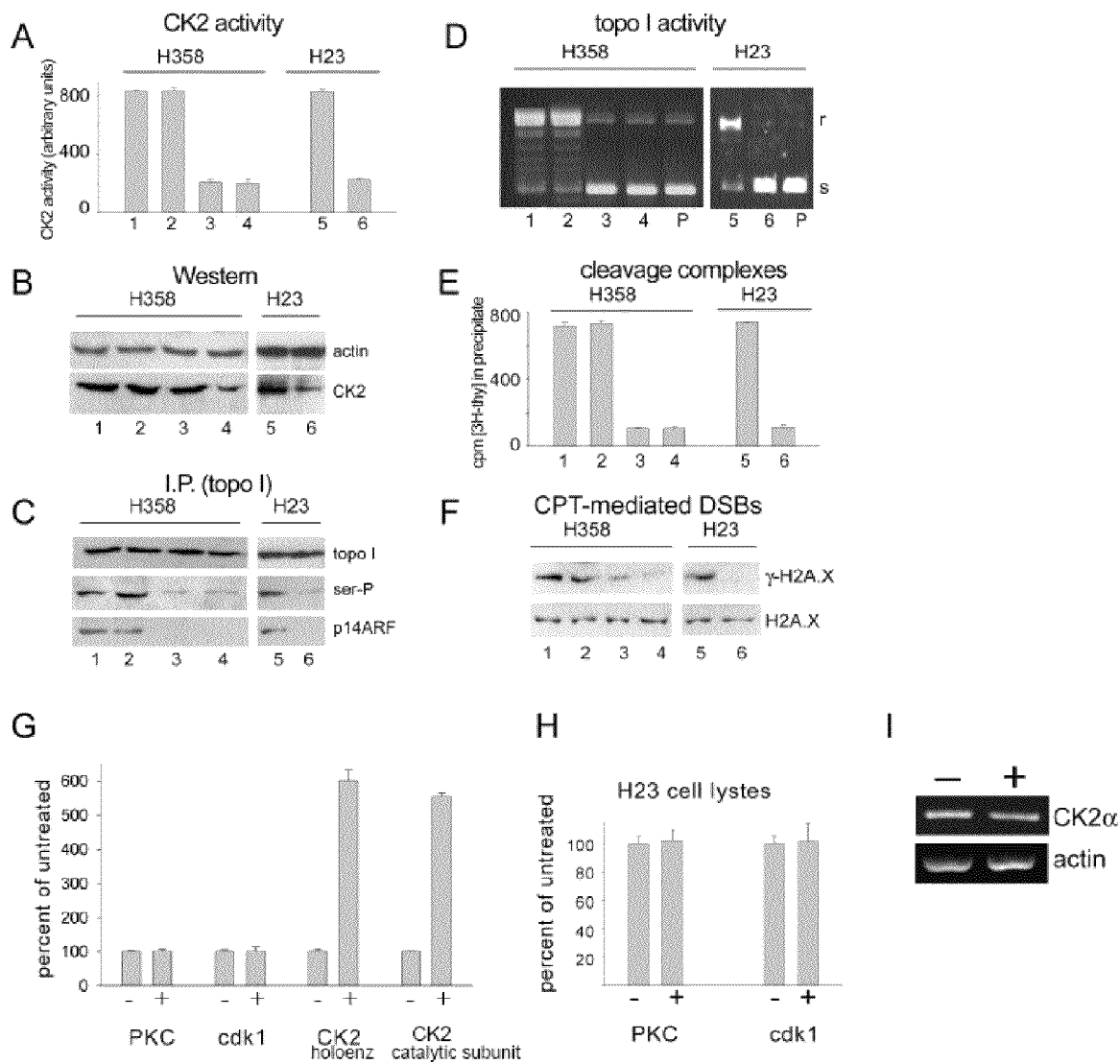
FIG. 15A shows a bar graph of assays of CK2 activity in nuclear extracts prepared from H358 cells (lanes 1-4) and H23 cells (lanes 5,6) 3 days after the following treatments: treated as follows: 1—no CK2 manipulation; 2—transfection with control, scrambled siRNA; 3—treatment 1 hour with 10 μM TBB; 4—transfection with CK2 siRNA; 5—treatment (for duration of assay) with CK2 activator; 6—no CK2 manipulation. Each assay represents the average of duplicate samples, with standard deviations shown.
FIG. 15B shows Western analysis of CK2 or actin (control) protein in lysates of H358 or H23 cells, 3 days after treatments in FIG. 15A.
FIG. 15C shows immunoprecipitations with anti-topo I of nuclear lysates of H358 or H23 cells, 3 days after treatments in FIG. 15A, followed by Western analysis of topo I (top row), phosphoserine (middle row), or p14ARF (bottom row) in the immunoprecipitated material.
FIG. 15D shows enzymatic assays of topoisomerase I-mediated conversion of supercoiled plasmid (S) to relaxed form (r) by nuclear extracts prepared from H358 or H23 cells 3 days after treatments in FIG. 15A. P=supercoiled plasmid only.
FIG. 15E shows bar graph of K+/SDS precipitation of covalent, camptothecin-stabilized cleavage complexes between topo I and cellular DNA of H358 or H23 cells. Cells were treated as in FIG. 15A, followed 3 days later by overnight labeling with [3H]-thymidine, followed by a 25 minute incubation in 0.08 μM camptothecin.
FIG. 15F shows Western analysis of γ-H2A.X and total H2A.X (control) in nuclear lysates of H358 and H23 cells, 3 days after the treatments in FIG. 15A.
FIG. 15G shows bar graph of purified CK2 holoenzyme (Promega, Madison, Wis.), CK2α1 catalytic subunit (Active Motif, Carlsbad, Calif.), PKC (Sigma, St. Louis, Mo.), and cdk1 (Enzo Life Sciences, Farmingdale, N.Y.) were assayed in vitro using assay kits purchased from Upsate Biotechnology/Millipore, Temecula, Calif.) in the absence (−) or presence (+) of 10 nM CK2 activator, 1-ethyl-4,5-dicarbamoylimidazole. 2 units of each enzyme were assayed.
FIG. 15H shows a bar graph where H23 cells were left untreated (−) or treated (+) with 10 nM CK2 activator, without changing the medium during the three day assay. Cell lysates were then prepared and assayed for PKC and cdk1 activity as described in Materials and Methods.
FIG. 15I shows H23 cells were left untreated (−) or exposed to 10 nM CK2 activator (+). RNA was isolated 3 days later using an RNA isolation kit (Qiagen, Valencia, Calif.) and RT-PCR was performed using CK2α primers and conditions described in Kramerov et al., Am J Pathol, 2006; 168:1722-1736, which produce a 151 bp DNA fragment revealed by ethidium bromide-stained agarose gel electrophoresis. Actin amplification of parallel aliquots served as a control. The results show that the CK2 activator did not act at the level of CK2α transcription.
Figure 16:
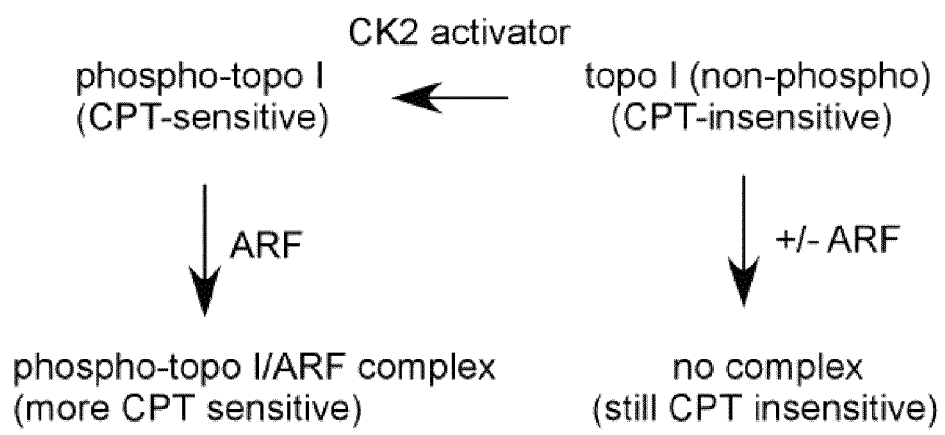
FIG. 16 shows a diagram summarizing an embodiment of how CK2 activators and/or ARF can be used to enhance camptothecin (CPT) sensitivity.

We down-regulated CK2 activity in H358 cells either by treating them with the highly selective CK2 inhibitor TBB (4,5,6,7-tetrabromobenzotriazole), which has minimal effects on PKC or cdk1 (Sarno, et al., Febs Lett 2001; 496: 44-48), or by downregulating CK2 expression using an siRNA mixture with specificity for the α and α' isoforms of the CK2 catalytic subunit. Conversely, we upregulated CK2 activity in H23 cells by treating them with a the CK2 activator, 1-ethyl-4,5-dicarbamoylimidazole (Reikhardt, et al., Neurosci Behav Physiol 2003; 22:799-804). The activator has a specific effect on purified CK2 activity, stimulating purified CK2 holoenzyme activity or CK2α catalytic subunit activity in vitro some 6-fold when used at the concentration used to treat cells (10 nM), while having no effect on either purified PKC and cdk1 activity or on endogenous PKC or cdk1 activity in treated H23 cells (FIGS. 15G and 15H, respectively). As shown by the bar graph in FIG. 15A, TBB or CK2 siRNA treatment of H358 cells reduces CK2 activity 72 hours later to some 25% of levels in untreated cells. A control scrambled sequence siRNA has no effect. CK2 activator treatment of H23 cells results in a 4-fold increase in CK2 activity relative to untreated H23 cells. A similar treatment of H358 cells results in only a 10% increase in CK2 activity (data not shown), suggesting that topo I in untreated H358 topo I is nearly maximally phosphorylated at potential CK2-targeted sites.

We carried out a Western analysis of CK2 protein (α subunit) in lysates of H358 and H23 cells 72 hours following the start of various treatments in FIG. 15A. As shown in the Western blot in FIG. 15B, TBB treatment of H358 cells has no effect on CK2 protein levels, as expected, but CK2 siRNA treatment of H358 cells reduces CK2 protein levels to about 47% of control levels (as determined by digital analyses of band intensities). CK2 activator treatment of H23 cells also enhances the accumulation of CK2 protein (FIG. 15B, lane 5), but not CK2α transcription (FIG. 15I), suggesting that the activator may promote increased translation or stabilization of CK2 protein though unknown mechanisms, in addition to its direct activation effect on purified CK2.

We then examined levels of total topo I protein, topo I serine phosphorylation, and topo I complex formation with p14ARF in H358 or H23 cells, treated as in FIG. 15A, by carrying out anti-topo I immunoprecipitations of nuclear extracts of treated cells, followed by Western analyses of topo I, phosphoserine, and p14ARF in the immunoprecipitated material (FIG. 15C). We found that total topo I protein levels are not affected by these treatments and remain similar in H358 and H23 cells (FIG. 15C, top panel), while the level of topo I phosphorylation and complex formation with p14ARF correlates with levels of CK2 activity (FIG. 15C, middle and lower panels, respectively). TBB or CK2-siRNA treatment of H358 cells reduces topo I serine phosphorylation to about 10% that of untreated H358 cells (as determined by digital quantitation of band intensities), indicating that the majority of topo I hyperphosphorylation is under CK2 control in these cells. Conversely, CK2 activator treatment of H23 cells increases topo I phosphorylation by some 4.7-fold relative to untreated H23 cells, as determined by digital quantitation of band intensities (FIG. 15C, middle panel), making it roughly equivalent to endogenous topo I phosphorylation levels in untreated H358 cells. Finally, a Western analysis of p14ARF in the topo I-immunoprecipitated material (FIG. 15C, bottom panel), shows that p14ARF/topo I complex formation occurs only in the presence of hyperphosphorylated topo I in both untreated H358 and CK2 activator-treated H23 cells. The results indicate that CK2-mediated phosphorylation has functional significance in vivo, consistent with our previous results in vitro (Bandyopadhyay, et al., Biochemistry 2007; 46:14325-14334).

We confirmed that the changes in topo I phosphorylation status correspond to the predicted changes in topo I activity by assaying nuclear extracts of H358 and H23 cells (untreated, or 72 hours after the treatments in FIG. 15A) for their ability to convert a supercoiled plasmid "s" to a relaxed form "r". FIG. 15D shows an ethidium bromide stained agarose gel following electrophoresis of the reaction products obtained from these assays. Under conditions where untreated H358 cell nuclear extract converts virtually all supercoiled plasmid form to relaxed form (0.75 μg lysate per reaction), essentially none is converted using nuclear extracts from H358 cells treated with TBB or CK2 siRNA, indicating that topo I activity is effectively inhibited in vivo by treatments that inhibit CK2 activity. Conversely, under conditions where nuclear extract from untreated H23 cells is essentially inactive (0.75 μg lysates protein per reaction), nuclear extract from CK2 activator-treated H23 cells converts virtually all of the supercoiled form to relaxed form, indicating that CK2 activation is sufficient to activate topo I activity to levels observed in H358 cells. Taken together, these results indicate that CK2 is necessary and sufficient to maintain topo I activity and function in these cancer cells.

The activation and suppression of topo I activity is predicted to produce a corresponding increase and decrease in camptothecin-induced DNA damage. Human topo I acts by introducing a single strand break in the DNA double helix via an intermediate covalent complex between the enzyme and DNA termed a "cleavable complex," in which an active tyrosyl residue at position 723 in the C-terminal domain of topo I becomes linked to the 3-end of the DNA break, leaving a 5'-OH on the other side of the break (see Champoux, Annu Rev Biochem 2001; 70:3690413), review). The passage of the non-cleaved strand unwinds the DNA by one linkage number and is followed by a resealing of the single strand break and release of the enzyme. Camptothecin and related drugs interact with the cleavage complex and stabilize it, so that DNA unwinding, resealing and enzyme release is prevented (Covey, et al., Cancer Res 1989; 49:5016-5022; Kjeldsen, et al., J Mol Biol 1992; 228:1025-1030; Koster, et al., Nature 2007; 448:213-217; Porter, and Champoux, Nucleic Acids Res 1989; 17:8521-8532; Svejstrup, et al., J Mol Biol 1991; 222:669-678). The single strand break can become a lethal double strand break upon passage of the replication fork (Hsiang, et al., Cancer Res 1989; 49:5077-5082). This mechanism, which converts topoisomerase I into a cellular poison, has been proposed to account for the cytotoxicity of camptothecin (Tsao, et al., Cancer Res 1993; 53:5908-5914), and explains why low levels of topoisomerase I, by limiting the frequency of cleavage complex formation, favor cell survival in the presence of camptothecin.

To determine levels of covalent cleavage complex formation, cells treated as in FIG. 15A, were DNA-labeled 72 hours later by overnight incubation in [$^3$H]-thymidine, followed by exposure to camptothecin to stabilize cleavage complexes, and K$^+$/SDS precipitation of covalent topo I-DNA cleavage complexes as described in Olnes and Kurl, Biotechniques 1994; 17:828-829.

Under these conditions of precipitation, only DNA covalently linked to topo I will co-precipitate with it. As shown by the bar graph of co-precipitated [$^3$H]-thymidine-labeled DNA in FIG. 15E, camptothecin-stabilized cleavage complexes are some 5 to 7-fold more frequent in cells expressing the highest levels of CK2 and phosphorylated topo I, indicating that more topo I molecules become associated with cellular DNA under these conditions.

Finally, since camptothecin treatment ultimately leads to the production of double strand DNA breaks (DSBs) in growing cells, we examined how the various treatments in FIG. 15A affect camptothecin-mediated induction of the phosphorylated form of the histone variant, H2A.X (denoted γ-H2A.X), which accumulates at sites of DSBs (Rogakou, et al., J Cell Biol 1999; 146:905-916). Total H2A.X served as a control. Camptothecin exposure was for 1 hour, initiated 72 hours after treatment of cells as in FIG. 15A. As shown in FIG. 15F, γ-H2A.X and hence, DNA double strand breaks, accumulates in camptothecin-treated cells expressing high levels of CK2 and phosphorylated topo I, confirming that the increased cellular sensitivity to camptothecin correlates with increased DNA damage.

Example 13

Camptothecin Sensitivity in Cancer Cells is Functionally Linked to CK2 Activity

Referring to FIGS. 13A and 13B, graphs are shown for experiments establishing a functional relationship between CK2 and the cellular response to camptothecin, further validating CK2 as a biomarker for therapy responsiveness. Experimental inhibition of CK2 in camptothecin-sensitive H358 cells makes these cells more resistant to camptothecin (FIG. 13A), and conversely, experimental activation of CK2 in camptothecin-resistant H23 cells makes them more sensitive to camptothecin (FIG. 13B). Experimental inhibition of CK2 in H358 cells was accomplished by pretreating them with 10 μM TBB (4,5,6,7-tetrabromobenzotriazole) for 1 hour (TBB purchased from Calbiochem), or by transducing them with an siRNA against CK2 (purchased from Upstate/Millipore). Both pretreatments were sufficient to reduce CK2 activity by about 75% over the 3-day period of the growth assay compared to cells that received no pretreatment or cells that were transduced with a control, scrambled siRNA. Experimental activation of CK2 in H23 cells was accomplished by maintaining cells in the presence of 10 nM of the CK2 activator, 1-ethyl-4,5-dicarbamoylimidazole (described in Reikhardt, et al. Neuroscience and Behavioral Physiology 2003; 33:799-804). This was the lowest dose (over the range of 5-100 nM) that could activate CK2 while having no effect on cell viability.

Example 14

Novel Topoisomerase I Phospho Epitope Identifies Camptothecin-Sensitive Cancer Cell Lines A novel CK2-mediated topo I phosphorylation site on serine 506 has been identified by a mass spectrometry analysis of purified baculovirus-expressed recombinant human topo I following dephosphorylation with alkaline phosphatase and extensive rephosphorylation with CK2. A rabbit polyclonal antibody was generated to a topo I peptide containing phosphoserine 506 (the sequence of the immunizing phosphopeptide is as follows: H-Thr-Val-Gly-Cys(Acm)-Cys(acm)-pSer-Leu-Arg-Val-Glu-His-Ile-Asn-Leu-His-Pro-Glu-Leu-lys-Lys-Cys-NH2 (SEQ ID NO: 7)). A control antibody was generated to the unphosphorylated peptide. The purified anti-topo I phosphoserine 506 IgG was found to be immunoreactive on Western blots with recombinant, baculovirus-expressed topo I that had been dephosphorylated with alkaline phosphates and rephosphorylated with CK2, but not with dephosphorylated topo I (FIG. 14A).

The anti-topo I phosphoserine 506 IgG was also found to be immunoreactive on Western blots with cellular topo I from the camptothecin-sensitive non small cell lung cancer Cell line, H358, but not with cellular topo I from the camptothecin-resistant non small cell lung cancer cell line, H23 (FIG. 14B). In contrast, the control IgG generated to the non-phosphorylated epitope reacted poorly with H383 topo I but strongly with H23 topo I (FIG. 14B).

Analysis of a broader array of human cancer cell lines, and two immortalized cell lines derived from normal human epithelial cells (Het1A) or human fibroblasts (BJ-1), showed that the phospho-specific antibody recognized cellular topo I from those cell lines that displayed sensitivity to camptothecin (FIG. 11A), namely H358, PC-3, DU145, LnCAP, OC3, and MDA MB 435 (abbreviated MB435). The camptothecin resistant cancer cell lines, H23 and HT29, and immortalized normal cell lines, BJ-1 and HET1A, expressed equivalent levels of topo I protein but it did not react with the phospho-specific antibody (FIG. 14C).

The phosphorylated epitope appears therefore to be a cancer-specific topo I abnormality directly related cellular sensitivity to topo I-targeted drugs. Furthermore, the anti-topo I phosphoserine 506 IgG can be used for immunofluorescence detection of phospho topo I in fixed, permeabilized H358 cells (FIG. 14D). This epitope can therefore be amenable to immunofluoresecence assays of fixed tumor specimens. This epitope is not present in normal cells, as shown by the Western blot in FIG. 14E of lysates of normal BJ1 human fibroblasts and normal HET1A human epithelial cells. A functional relationship between CK2 and the phosphoserine 506 epitope was demonstrated in the Western blots in FIG. 14F by showing that activation of CK2 in H23 cells treated with the CK2 activator as in FIG. 13B induces cellular levels of the phosphorylated epitope, detected with the anti-topo I phosphoserine 506 IgG (FIG. 14F, upper panel) and inhibition of CK2 in H358 cells treated with TBB as in FIG. 13A suppresses cellular levels of the phosphoserine epitope, detected with the anti-topo I phosphoserine 506 IgG (FIG. 14F, upper panel). Total topoisomerase I levels served as a control (lower panel, FIG. 14F).

Example 15

CK2 mRNA Levels are Upregulated in Camptothecin-Sensitive Cancer Cells

FIG. 12 shows the result of a semi quantitative PCR of CK2 mRNA levels. Analysis of CK2 mRNA levels in cellular RNA, normalized to levels in HET1A cells, showed that levels in normal cells (HET1A, BJ-1, GT41F) and the 3 camptothecin-resistant cancer cell lines (H23, HT29, SW480) are lower than levels in the 6 camptothecin-sensitive cancer cell lines (H358, PC3, DU145, LnCAP, MDAMB-435, OC3). Digital quantitation of band intensities for CK2 are shown below the lanes. RNA was isolated using a RNA isolation kit (Qiagen, Valencia, Calif.) and RT-PCR was performed using CK2α primers and conditions described in Kramerov et al., Am J Pathol, 2006; 168:1722-1736, which produce a 151 bp DNA fragment revealed by ethidium bromide-stained agarose gel electrophoresis. Actin amplification of parallel aliquots served as a control. The results show that the CK2 activator did not act at the level of CK2α transcription.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation; and there is no intention in the use of such terms and expressions of excluding any equivalents of the features shown and described or portions thereof, but it is recognized that various modifications are possible within the scope of the invention claimed.

Thus, it should be understobd that although the invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for treating cancer in a patient, comprising:
   (i) determining status of phosphorylation, by way of an assay, on serine 506 amino acid residue of topoisomerase I in a biological specimen from said patient;
   (ii) identifying said patient as being sensitive to a topoisomerase I inhibitor when phosphorylation of serine 506 amino acid residue of topoisomerase I is above a predetermined threshold as determined by said assay; and
   (iii) administering the topoisomerase I inhibitor to said patient.

2. The method of claim 1, wherein the predetermined threshold is a ratio of unphosphorylated topoisomerase I to phosphorylated topoisomerase I within said biological sample.

3. The method of claim 2, wherein said patient is identified as being sensitive to the topoisomerase I inhibitor when the ratio is less than 1, and said patient is identified as being resistant to the topoisomerase I inhibitor when the ratio is greater than 1.

4. The method of claim 1, wherein the biological specimen is selected from the group consisting of tumor cells, tumor tissue, blood, serum, urine, and sputum.

5. The method of claim 1, wherein said topoisomerase I inhibitor is selected from the group consisting of camptothecin, irinotecan, topotecan, an analogue thereof, or a non-camptothecin-derived topoisomerase I inhibitor.

6. The methods of claim 1, wherein said cancer is selected from the groups consisting of lung cancer, prostate cancer, hepatocellular carcinoma, breast cancer, colorectal cancer, acute myelogenous leukemia, melanoma, ovarian cancer, neuroendocrine carcinoma, gastric cancer, esophageal cancer, pancreatic cancer, adenocarcinoma, brain cancer, head and neck cancer, bone marrow-derived cancer, bone cancer, kidney cancer, retina cancer, bladder cancer, liver cancer, and mesothelioma cancer.

* * * * *